(12) United States Patent
Doi et al.

(10) Patent No.: US 7,820,423 B2
(45) Date of Patent: Oct. 26, 2010

(54) METHOD AND A SYSTEM FOR PREDICTING PROTEIN FUNCTIONAL SITE, A METHOD FOR IMPROVING PROTEIN FUNCTION, AND A FUNCTION-MODIFIED PROTEIN

(75) Inventors: Hirofumi Doi, Chiba (JP); Hideaki Hiraki, Tokyo (JP); Akio Kanai, Ibaraki (JP)

(73) Assignee: Japan Science And Technology Corporation, Saitama (JP)

( * ) Notice: Subject to any disclaimer, the term of this patent is extended or adjusted under 35 U.S.C. 154(b) by 454 days.

(21) Appl. No.: 11/806,448

(22) Filed: May 31, 2007

(65) Prior Publication Data

US 2008/0262201 A1 Oct. 23, 2008

Related U.S. Application Data

(60) Division of application No. 10/345,205, filed on Jan. 16, 2003, now Pat. No. 7,231,301, which is a continuation of application No. 09/697,138, filed on Oct. 27, 2000, now abandoned, which is a continuation-in-part of application No. 09/355,486, filed as application No. PCT/JP98/00430 on Feb. 2, 1998, now abandoned.

(30) Foreign Application Priority Data

| Jan. 31, 1997 | (JP) | 1997-019248 |
|---|---|---|
| Jan. 31, 1997 | (JP) | 1997-019249 |
| Dec. 2, 1997 | (JP) | 1997-332100 |
| Jan. 30, 1998 | (JP) | 1998-018699 |

(51) Int. Cl.
*C12N 9/12* (2006.01)
(52) U.S. Cl. .................. 435/194; 435/483
(58) Field of Classification Search .............. None
See application file for complete search history.

(56) References Cited

U.S. PATENT DOCUMENTS 5,489,523 A * 2/1996 Mathur ................ 435/194

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Zhang et al., From fold predictions to function predictions: Automation of functional site conservation analysis for functional genome predictions, Protein Science, vol. 8, No. 5, pp. 1104-1115 (1999).
Tatusov et al., "Metabolism and evolution of Haemophilus influenzae deduced from whome-genome comparision with *Escherichia coli*", Current Biology vol. 6, No. 3, pp. 279-291 (1996).

* cited by examiner

*Primary Examiner*—Richard G Hutson
(74) *Attorney, Agent, or Firm*—Wenderoth, Lind & Ponack, L.L.P

(57) ABSTRACT

The present application provides a method for predicting the functional site of a protein using data of the entire proteins of an organism of which genome data or cDNA data is known. More specifically, the present application provides a method for predicting a protein functional site, comprising the steps of calculating the frequency of occurrence of an oligopeptide in the entire proteins, calculating the value of each amino-acid residue contributing to the frequency of occurrence as the representative value of the function, and predicting the protein functional site by using the representative value of function as an indicator. The present also provides a system for predicting a functional site for automatically performing said methods. Additionally, the present application provides a method for preparing a function-modified protein comprising subjecting the amino-acid residues composing the functional site identified by the method described above to artificial mutation, and a novel thermophilic DNA polymerase prepared by the method.

1 Claim, 24 Drawing Sheets motif A

MJ0558 Position 325..346 motif C

MJ0558 Position 550..570

Fig. 17 motif C

```
              550                    570
MJ   AEKFGFKVLYIDTDGFYAIWK
KOD  EEKYGFKVIYSDTDGFFATIP
Pfu  EEKFGFKVLYIDTDGLYATIP
```

METHOD AND A SYSTEM FOR PREDICTING PROTEIN FUNCTIONAL SITE, A METHOD FOR IMPROVING PROTEIN FUNCTION, AND A FUNCTION-MODIFIED PROTEIN

This application is a divisional application of Ser. No. 10/345,205, filed Jan. 16, 2003, now U.S. Pat. No. 7,231,301, which is a Continuation of Ser. No. 09/697,138, filed Oct. 27, 2000, now abandoned, which is a Continuation-In-Part of Ser. No. 09/355,486, filed Sep. 20, 1999, now abandoned, which is a 371 of PCT/JP98/00430, filed Feb. 2, 1998, the teachings of the above-referenced applications are hereby incorporated by reference.

TECHNICAL FIELD

The present invention relates to a method for predicting a functional site of a protein, a system for predicting the function thereof, and a method for modifying the function of a protein and a function-modified protein. More specifically, the present invention relates to prediction of a functional site of a functionally unknown protein prepared by genome analysis or cDNA analysis, prediction of a novel function and a novel functional site of a protein with a known function, and prediction of a site on a protein to be modified for improving the function of the protein, and a protein with a modified function based on the prediction.

BACKGROUND ART

Following the progress of genome analysis and cDNA analysis of various organisms including pathogenic microorganisms, the number of novel genes whose functions are unknown is rapidly increasing, together with the number of proteins encoded by the genes. So far, the analysis of the nucleotide sequence of the whole genome of a microorganism, for example *Mycoplasma genitalium* (Fraser et al., Science 270, 397-403, 1995), *Haemophilus influenzae* (Fleischman et al., Science 269, 496-512, 1995), and *Methanococcus jannaschii* (Bult et al., Science 273, 1058-1073, 1996), has been completed, so that numerous novel proteins predicted from the genome sequence have been discovered. For humans and mice, the cDNA analysis is under way in combination with the genome analysis, which brings about the discovery of a great number of novel proteins.

In such circumstance, the prediction of the function of a functionally unknown protein or a functional site thereof has been a significant issue. If not only a novel protein but also a novel function or a novel functional site of a protein with a known function is discovered, whether or not these proteins are worth industrial or clinical application is possibly determined. Furthermore, such prediction of function possibly enables to prepare a modified protein with a further improved function.

Whether or not a protein encoded by a gene elucidated by genome analysis or cDNA analysis is novel or has a known function has been determined conventionally by searching the homology through protein databases such as Swiss-Prot. So as to predict a functional site, additionally, functionally identical proteins derived from various organisms are extracted from a protein database and are then subjected to alignment, to identify a region conserved in common to them and predict the conserved region as a functional site.

However, disadvantageously, such alignment method cannot be used if a protein obtained by genome analysis or cDNA analysis is an absolutely novel protein. Even if the protein has homology with known proteins in a protein database, the conserved region occupies most of the amino acid sequence of the protein in case that the protein is homologous to proteins derived from closely related organisms, so that it is impossible to predict the functional site. As to modification of protein, generally, the function of a protein is potentially deteriorated irrespective of the fact that the function is known or unknown once the conserved region is modified, even if the functional site is predicted by alignment. Accordingly, the amino-acid residues outside the conserved region should be modified to improve the function. In other words, it is required to find a novel functional site in such protein to be modified. Using the conventional alignment method, disadvantageously, a novel functional site cannot be discovered or which amino-acid residue should be modified cannot be predicted.

Taking account of such circumstance, the present invention has been carried out. It is an object of the present invention to provide a novel method for predicting a functional site of a functionally unknown protein obtained by genome analysis or cDNA analysis.

In accordance with the present invention, furthermore, it is an object to provide a system for predicting the function.

In accordance with the present invention, still furthermore, it is an object to provide a method for predicting a novel functional site of a protein with an unknown function or with a known function and subjecting the functional site to mutation to prepare a modified protein.

Still furthermore, it is an object of the present invention to provide a protein with a function modified by the method described above.

DISCLOSURE OF INVENTION

A first aspect of the present invention proposed by the present application is a method for predicting a functional site of a protein derived from an organism "a" whose genome data, therefore the entire putative proteins, or cDNA data is known, which method comprises the steps of:

(1) determining in the amino acid sequences of the entire proteins of the organism "a", the frequency of occurrence of each amino acid and the frequency of occurrence of individual oligopeptides produced by permutations of twenty amino acids, and determining the smallest length (n) of oligopeptides satisfying the following criteria;

among oligopeptides of length (n), the number of oligopeptides which occur once in the entire proteins is smaller than the number of oligopeptides which occur twice in the entire proteins; among oligopeptides of length (n+1), the number of oligopeptides which occur once in the entire proteins is larger than the number of oligopeptides which occur twice in the entire proteins, (2) determining in the entire proteins of the organism "a", the frequency of occurrence of the following Aji-oligopeptide of length (n+1), which is a part of the amino acid sequence of the protein as a subject for predicting a functional site and contains the j-th amino-acid residue Aj from the amino terminal end (N-terminus) of the amino acid sequence (length of L) of the protein, on condition that the j-th amino-acid residue Aj is defined as the i-th residue Aji from the N-terminus of the Aji-oligopeptide;

Aji-oligopeptide: aj1aj2 ... Aji ... ajnaj(n+1)

(wherein, $1 \leq i \leq n+1$; $n+1 \leq j \leq L-n$; Aj=Aji; and Aji is the i-th residue of the oligopeptide; and moreover, aj1=Aj−i+1, ..., aj(n+1)=Aj−i+(n+1)), and determining in the entire proteins of the organism "a", the frequency of occurrence of the following Xji-oligopeptide of length (n+1);

Xji-oligopeptide: aj1aj2 ... Xji ... ajnaj(n+1)

(wherein, $1 \leq i \leq n+1$; $n+1 \leq j \leq L-n$; and the i-th amino-acid residue Xji is any amino acid; and moreover, aj1=Aj−i+1, ..., aj(n+1)=Aj−i+(n+1)), (3) calculating ratio Yji of the frequency of occurrence of the Aji-oligopeptide to that of the Xji-oligopeptide, (4) determining mean Yj of the Yji;

$$Yj = \sum_{i=1}^{n+1} Yji/(n+1),$$

(5) determining functional value Zj of Yj;

$$Zj=f(Yj)$$

(Function f is a monotonously decreasing function or a monotonously increasing function), and defining the Zj value as the representative value of the function of the j-th amino-acid residue Aj of the amino acid sequence (length of L), and (6) repeating the steps (2) to (5) sequentially and determining the Zj value of each Aj of all the amino-acid residues at positions between $n+1 \leq j \leq L-n$ in the amino acid sequence (length of L) of the protein, thereby predicting the degree of the involvement of each amino-acid residue in the function of the protein by using the dimension of the Zj value as an indicator.

A second aspect of the present invention is a method for predicting a functional site of a protein derived from the entire putative proteins of an organism "a" of which genome data or cDNA data is known, which method comprises the steps of:

(1) determining the frequency of occurrence of each amino acid and the frequency of occurrence of individual oligopeptides produced by permutations of twenty amino acids, in the amino acid sequences of the entire proteins of the organism "a", (2) as to an appropriate protein of the organism "a", (2') determining in the entire proteins of the organism "a", the frequency of occurrence of the following Aji-oligopeptide of given length of (n) ($1 \leq n \leq M$, provided that M is the smallest length of oligopeptides satisfying the criterion that all the oligopeptides of length M are at frequency 1 of the occurrence), which the Aji-oligopeptide is a part of the amino acid sequence of the protein and contains the j-th amino-acid residue Aj, on condition that the j-th amino-acid residue Aj is defined as the i-th residue Aji from the N-terminus of the Aji-oligopeptide ($n \leq j \leq L-n+1$);

Aji-oligopeptide: aj1aj2 ... Aji ... ajn (wherein, $1 \leq i \leq n$; Aj=Aji, and Aji is the i-th residue of the oligopeptide; and moreover, aj1=Aj−i+1, ..., ajn=Aj−i+n), and determining in the entire proteins of the organism "a", the frequency of occurrence of the following Xji-oligopeptide of length (n) corresponding to the length of Aji-oligopeptide;

Xji-oligopeptide: aj1aj2 ... Xji ... ajn (wherein, $1 \leq i \leq n$; and the i-th residue Xji is any amino acid; and moreover, aj1=Aj−i+1, ..., ajn=Aj−i+n), (3) calculating ratio Yji of the frequency of occurrence of the Aji-oligopeptide to that of the Xji-oligopeptide, (4) determining mean Y(j,n) of the Yji;

$$Y(j,n) = \sum_{i=1}^{n} Yji/n,$$

(5) determining functional value Z(j,n) of Y(j,n);

$$Z(j,n)=-\log(Y(j,n)),$$

(6) repeating the steps (2') to (5) sequentially and determining the Z(j,n) value of each amino-acid residue Aj at position j ($n \leq j \leq L-n+1$) in the amino acid sequence (length of L), (7) sequentially repeating the steps (2) to (6) for the entire proteins of the organism "a", thereby determining the distribution of the Z(j,n) value of each amino-acid residue in the entire proteins, and the Z(j,n) values are classified into twenty according to the twenty amino acids, and then determining mean Av(Aa) of the Z(j,n) values for each amino acid Aa and the standard deviation Sd (Aa) of the distribution thereof, on the basis of the distribution, to determine function g to the j-th amino-acid residue Aj of a protein for normalizing the difference in distribution due to the species of amino-acid residues;

$$g=g(Z(j,n),Aj)=[Z(j,n)-Av(Aa)]/Sd(Aa)$$

(provided that Aj=Aa; and $1 \leq n \leq M$), (8) determining value D(j,n) of the function g of each Aj of all the amino-acid residues at position j ($n \leq j \leq L-n+1$ and $1 \leq n \leq M$) of a protein in the entire proteins as recovered in the step (7);

$$D(j,n)=g(Z(j,n),Aj),$$

and (9) defining the representative value of the function of the j-th amino-acid residue in the amino acid sequence (length of L) as functional value Wj of the Z(j,n) and D(j,n);

$$Wj=h(Z(j,1),Z(j,2), ..., Z(j,M),D(j,1),D(j,2), ..., D(j,M))$$

thereby predicting the degree of the involvement of each amino-acid residue in the function of the protein by using the dimension of the Wj value as an indicator.

A third aspect of the present invention is a system for automatically conducting the method according to claim 1, at least comprising the following units (a) to (g);

(a) an outer memory unit memorizing the amino acid sequence data of the entire putative proteins derived from organism "a" of which genome data or cDNA data is known, as well as an existing protein data base, (b) a calculation/memory unit, composed of CPU calculating the frequency of occurrence of each amino acid and the frequency of occurrence of individual oligopeptides produced by permutations of twenty amino acids, in the amino acid sequences of the entire proteins from the organism "a", and a memory unit having the memory of the calculation results, (c) a calculation/memory unit, composed of CPU calculating the smallest length (n) of oligopeptide satisfying the following criteria among the individual oligopeptides of which the frequencies of the occurrences being memorized in the unit (b);

among oligopeptides of length (n), the number of oligopeptides which occur once in the entire proteins is smaller than the number of oligopeptides which occur twice in the entire proteins; among oligopeptides of length (n+1), the number of oligopeptides which occur once in the entire proteins is larger than the number of oligopeptides which occur twice in the entire proteins, and a memory unit having the memory of the length (n), (d) a calculation/memory unit, composed of CPU determining in the entire proteins of the organism "a", the frequency of occurrence of the following Aji-oligopeptide of length (n+1), which is a part of the amino acid sequence of the protein as a subject for predicting a functional site and contains the j-th amino-acid residue Aj from the amino terminal end (N-terminus) of the amino acid sequence (length of L) of the protein, on condition that the j-th amino-acid residue Aj is defined as the i-th residue Aji from the N-terminus of the Aji-oligopeptide;

Aji-oligopeptide: aj1aj2 ... Aji ... ajnaj(n+1)

(wherein, $1 \leq i \leq n+1$; $n+1 \leq j \leq L-n$; Aj=Aji; and Aji is the i-th residue of the oligopeptide; and moreover, aj1=Aj−i+1, ..., aj(n+1)=Aj−i+(n+1)), and determining in the entire proteins of the organism "a", the frequency of occurrence of the following Xji-oligopeptide of length (n+1);

Xji-oligopeptide: aj1aj2 ... Xji ... ajnaj(n+1)

(wherein, $1 \leq i \leq n+1$; $n+1 \leq j \leq L-n$; and the i-th amino-acid residue Xji is any amino acid; and moreover, aj1=Aj−i+1, ..., aj(n+1)=Aj−i+(n+1)), and a memory unit having the memory of the calculation results, (e) a calculation/memory unit, composed of CPU determining ratio Yji of the frequency of occurrence of the Aji-oligopeptide to that of the Xji-oligopeptide, and a memory unit having the memory of Yji, (f) a calculation/memory unit, composed of CPU determining mean Yj of the Yji;

$$Yj = \sum_{i=1}^{n+1} Yji/(n+1),$$

and a memory unit having the memory of Yj, and (g) a calculation/memory unit, composed of CPU determining functional value Zj of Yj;

$Zj=f(Yj)$ (Function f is a monotonously decreasing function or a monotonously increasing function), and a memory unit having the memory of Zj.

A fourth aspect of the present invention is a system for automatically conducting the method according to claim 3, at least comprising the following units (a) to (i);

(a) an outer memory unit memorizing the amino acid sequence data of the entire putative proteins of the organism "a" of which genome data or cDNA data is known, as well as an existing protein data base, (b) a calculation/memory unit, composed of CPU calculating in the amino acid sequences of the entire proteins of the organism "a", the frequency of occurrence of each amino acid and the frequency of occurrence of individual oligopeptides produced by permutations of twenty amino acids, and a memory unit having the memory of the calculation results, (c) a calculation/memory unit, composed of CPU determining in the entire proteins of the organism "a", the frequency of occurrence of the following Aji-oligopeptide of given length of (n) ($1 \leq n \leq M$, provided that M is the smallest length of oligopeptides satisfying the criterion that all the oligopeptides of length M are at frequency 1 of the occurrence), which the Aji-oligopeptide is a part of the amino acid sequence of the protein and contains the j-th amino-acid residue Aj, on condition that the j-th amino-acid residue Aj is defined as (or identical to?) the i-th residue Aji from the N-terminus of the Aji-oligopeptide ($n \leq j \leq L-n+1$);

Aji-oligopeptide: aj1aj2 ... Aji ... ajn (wherein, $1 \leq i \leq n$; Aj=Aji, and Aji is the i-th residue of the oligopeptide; and moreover, aj1=Aj−i+1, ..., ajn=Aj−i+n), and determining in the entire proteins of the organism "a", the frequency of occurrence of the following Xji-oligopeptide of length (n) corresponding to the length of Aji-oligopeptide;

Xji-oligopeptide: aj1aj2 ... Xji ... ajn (wherein, $1 \leq i \leq n$; and the i-th residue Xji is any amino acid; and moreover, aj1=Aj−i+1, ..., ajn=Aj−i+n), and a memory unit memorizing the calculation results, (d) a calculation/memory unit, composed of CPU calculating ratio Yji of the frequency of occurrence of the Aji-oligopeptide to that of the Xji-oligopeptide, and a memory unit having the memory of the Yji, (e) a calculation/memory unit, composed of CPU determining mean Y(j,n) of the Yji;

$$Y(j, n) = \sum_{i=1}^{n} Yji/n,$$

and a memory unit having the memory of Y(j,n), (f) a calculation/memory unit, composed of CPU determining functional value Z(j,n) of Y(j,n);

$Z(j,n)=-\log(Y(j,n))$, and a memory unit having the memory of Z(j,n), (g) a calculation/memory unit, composed of CPU determining the distribution of the Z(j,n) value of each amino-acid residue in the entire proteins, and the Z(j,n) values are classified into twenty according to the twenty amino acids, and then determining mean Av(Aa) of the Z(j,n) values for each amino acid Aa and the standard deviation Sd (Aa) of the distribution thereof, on the basis of the distribution, to determine function g to the j-th amino-acid residue Aj of a protein for normalizing the difference in distribution due to the species of amino-acid residues;

$g=g(Z(j,n),Aj)=[Z(j,n)-Av(Aa)]/Sd(Aa)$ (wherein, Aj=Aa; and $1 \leq n \leq M$)

and a memory unit having the memory of g, (h) a calculation/memory unit, composed of CPU determining value D (j,n) of function g memorized in the unit (g) concerning each of all the amino-acid residues Aj at position j ($n \leq j \leq L-n+1$) in the amino acid sequence (length of L);

$D(j,n)=g(Z(j,n),Aj)$ and a memory unit having the memory of the D(j, n) value, and (i) a calculation/memory unit, composed of a calculation unit determining appropriate functional value Wj of the Z(j,n) and D(j,n) of each amino-acid residue in the amino acid sequence;

$Wj=h(Z(j,1),Z(j,2), ..., Z(j,M),D(j,1),D(j,2), ..., D(j,M))$ and a memory unit having the memory of the Wj value.

A fifth aspect of the present invention is a method for modifying the known function of protein "A" derived from the entire proteins of organism "a" of which genome data or cDNA data has been known, which method comprises the steps of:

(1) extracting a protein closely related to the protein "A" from an existing protein data base and subjecting the proteins to alignment, (2) determining in the amino acid sequences of the entire proteins of the organism "a", the frequency of occurrence of each amino acid and the frequency of occurrence of individual oligopeptides produced by permutations of twenty amino acids, and determining the smallest length (n) of oligopeptides satisfying the following criteria;

among oligopeptides of length (n), the number of oligopeptides which occur once in the entire proteins is smaller than the number of oligopeptides which occur twice in the entire proteins; among oligopeptides of length (n+1), the number of oligopeptides which occur once in the entire proteins is larger than the number of oligopeptides which occur twice in the entire proteins, (3) determining in the entire proteins of the organism "a", the frequency of occurrence of the following Aji-oligopeptide of length (n+1), which is a part of the amino acid sequence of the protein as a subject for predicting a functional site and contains the j-th amino-acid residue Aj from the amino terminal end (N-terminus) of the amino acid sequence (length of L) of the protein, on condition that the j-th amino-acid residue Aj is defined as the i-th residue Aji from the N-terminus of the Aji-oligopeptide;

Aji-oligopeptide: aj1aj2 ... Aji ... ajnaj(n+1)

(wherein, $1 \leq n+1$; $n+1 \leq j \leq L-n$; $Aj=Aji$; and Aji is the i-th residue of the oligopeptide; and moreover, $aj1=Aj-i+1, \ldots, aj(n+1)=Aj-i+(n+1)$), and determining in the entire proteins of the organism "a", the frequency of occurrence of the following Xji-oligopeptide of length (n+1);

Xji-oligopeptide: aj1aj2 ... Xji ... ajnaj(n+1)

(wherein, $1 \leq n+1$; $n+1 \leq j$ $L-n$; and the i-th amino-acid residue Xji is any amino acid, and moreover, $aj1=Aj-i+1, \ldots, aj(n+1)=Aj-i+(n+1)$), (4) calculating ratio Yji of the frequency of occurrence of the Aji-oligopeptide to that of the Xji-oligopeptide, (5) determining mean Yj of the Yji;

$$Yj = \sum_{i=1}^{n+1} Yji/(n+1),$$

(6) determining functional value Zj of Yj;

$Zj=f(Yj)$ (Function f is a monotonously decreasing function or a monotonously increasing function), and defining the Zj value as the representative value of the function of the j-th amino-acid residue Aj of the amino acid sequence (length of L) of the protein "A", (7) sequentially repeating the steps (3) to (6) and determining the Zj value of each of all the amino-acid residues at positions between $n+1 \leq j \leq L-n$ in the amino acid sequence (length of L) of the protein "A", (8) selecting at least one amino-acid residue to be subjected to mutation from the amino acid sequence (length of L) of the protein "A" on the basis of the alignment data carried out in the step (1), sequentially repeating the steps (3) to (6) for variant amino-acid residues in various mutated (or mutant?) amino acid sequences where the selected amino-acid residue has been mutated into another amino-acid residue, to determine the Zj value of the variant amino-acid residues, (9) selecting a mutated amino acid sequence wherein the Zj value of the variant amino-acid residue as determined in the step (8) is larger or smaller than the Zj value of the wild type amino-acid residue as determined in the step (7), and

(10) preparing a modified gene encoding the modified amino acid sequence from the protein "A" gene, and producing the modified protein as the expression product of the gene.

A sixth aspect of the present invention is a method for modifying the function of protein "B" derived from an organism "b" of which genome data or cDNA data has been unknown, which method comprises the steps of:

(1) extracting protein "A" most closely related to protein "B" from the entire proteins of organism "a" of which genome data or cDNA data being known and subjecting the protein to alignment, or extracting a protein closely related to protein "B" from an existing protein data base to subject the protein to alignment, (2) determining in the amino acid sequences of the entire proteins of the organism "a", the frequency of occurrence of each amino acid and the frequency of occurrence of individual oligopeptides produced by permutations of twenty amino acids, and determining the smallest length (n) of oligopeptides satisfying the following criteria;

among oligopeptides of length (n), the number of oligopeptides which occur once in the entire proteins is smaller than the number of oligopeptides which occur twice in the entire proteins; among oligopeptides of length (n+1), the number of oligopeptides which occur once in the entire proteins is larger than the number of oligopeptides which occur twice in the entire proteins, (3) determining in the entire proteins of the organism "a", the frequency of occurrence of the following Aji-oligopeptide of length (n+1), which is a part of the amino acid sequence of the protein as a subject for predicting a functional site and contains the j-th amino-acid residue Aj from the amino terminal end (N-terminus) of the amino acid sequence (length of L) of the protein, on condition that the j-th amino-acid residue Aj is defined as the i-th residue Aji from the N-terminus of the Aji-oligopeptide;

Aji-oligopeptide: aj1aj2 ... Aji ... ajnaj(n+1)

(wherein, $1 \leq i \leq n+1$; $n+1 \leq j \leq L-n$; $Aj=Aji$; and Aji is the i-th residue of the oligopeptide; and moreover, $aj1=Aj-i+1, \ldots, aj(n+1)=Aj-i+(n+1)$), and determining in the entire proteins of the organism "a", the frequency of occurrence of the following Xji-oligopeptide of length (n+1);

Xji-oligopeptide: aj1aj2 ... Xji ... ajnaj(n+1)

(wherein, $1 \leq i \leq n+1$; $n+1 \leq j \leq L-n$; and the i-th amino-acid residue Xji is any amino acid; and moreover, $aj1=Aj-i+1, \ldots, aj(n+1)=Aj-i+(n+1)$), (4) calculating ratio Yji of the frequency of occurrence of the Aji-oligopeptide to that of the Xji-oligopeptide, (6) determining mean Yj of the Yji;

$$Yj = \sum_{i=1}^{n+1} Yji/(n+1),$$

(6) determining functional value Zj of Yj;

$Zj=f(Yj)$ (Function f is a monotonously decreasing function or a monotonously increasing function), and defining the Zj value as the representative value of the function of the j-th amino-acid residue Aj of the amino acid sequence (length of L) of the protein "A", (7) sequentially repeating the steps (3) to (6) and determining the Zj value of each of all the amino-acid residues at positions between $n+1 \leq j \leq L-n$ in the amino acid sequence (length of L), (8) selecting at least one amino-acid residue to be subjected to mutation from the amino acid sequence (length of L) of the protein "A" on the basis of the alignment data carried out in the step (1), sequentially repeating the steps (3) to (6) for variant amino-acid residues in various mutated amino acid sequences where the selected amino-acid residue has been mutated into another amino-acid residues, to determine the Zj value of the variant amino-acid residues, (9) selecting the mutation position and the mutated amino-acid residue wherein the Zj value of the variant amino-acid residue as determined in the step (8) is larger or smaller than the Zj value of the wild type amino-acid residue as determined in the step (7), and

(10) preparing a modified gene encoding the modified amino acid sequence having the mutated amino-acid residue at the position from the protein "B" gene, and producing the modified protein as the expression product of the gene.

A seventh aspect of the present invention is a method for modifying the known function of protein "A" derived from the entire proteins of organism "a" of which genome data or cDNA data has been known, which method comprises the steps of:

(1) extracting proteins closely related to the protein "A" from an existing protein data base and subjecting the proteins to alignment, (2) determining the frequency of occurrence of each amino acid and the frequency of occurrence of individual oligopeptides produced by permutations of twenty amino acids, in the amino acid sequences of the entire proteins of the organism "a", (3) as to an appropriate protein of the organism "a", (3') determining in the entire proteins of the organism "a", the frequency of occurrence of the following Aji-oligopeptide of given length of (n) ($1 \leq n \leq M$, provided that M is the smallest length (n) of oligopeptides satisfying the criterion that all the oligopeptides of length M are at frequency 1 of the occurrence), which the Aji-oligopeptide is a part of the amino acid sequence of the protein and contains the j-th amino-acid residue Aj, on condition that the j-th amino-acid residue Aj is defined as the i-th residue Aji from the N-terminus of the Aji-oligopeptide ($n \leq j \leq L-n+1$);

Aji-oligopeptide: aj1aj2 ... Aj ... ajn (wherein, $1 \leq i \leq n$; Aj=Aji, and Aji is the i-th residue of the oligopeptide; and moreover, aj1=Aj-i+1, ..., ajn=Aj-i+n), and determining in the entire proteins of the organism "a", the frequency of occurrence of the following Xji-oligopeptide of length (n) corresponding to the length of Aji-oligopeptide;

Xji-oligopeptide: aj1aj2 ... Xji ... ajn (wherein, $1 \leq i \leq n$; and the i-th residue Xji is any amino acid; and moreover, aj1=Aj-i+1, ..., ajn=Aj-i+n), (4) calculating ratio Yji of the frequency of occurrence of the Aji-oligopeptide to that of the Xji-oligopeptide, (5) determining mean Y(j,n) of the Yji;

$$Y(j, n) = \sum_{i=1}^{n} Yji/n,$$

(6) determining functional value Z(j,n) of Y(j,n);

$Z(j,n)=-\log(Y(j,n))$, (7) repeating the steps (3') to (6) sequentially and determining the Z(j,n) value of each amino-acid residue Aj at position j ($n \leq j \leq L-n+1$) in the amino acid sequence (length of L), (8) sequentially repeating the steps (3) to (7) for the entire proteins of the organism "a", thereby determining the distribution of the Z(j,n) value of each amino-acid residue in the entire proteins, and the Z(j,n) values are classified into twenty according to the twenty amino acids, and then determining mean Av(Aa) of the Z(j,n) values for each amino acid Aa and the standard deviation Sd (Aa) of the distribution thereof, on the basis of the distribution, to determine function g to the j-th amino-acid residue Aj of a protein for normalizing the difference in distribution due to the species of amino-acid residues;

$g=g(Z(j,n),Aj)=[Z(j,n)-Av(Aa)]/Sd(Aa)$ (provided that Aj=Aa; and $1 \leq n \leq M$), (9) determining value D (j,n) of the function g of each Aj of all the amino-acid residues at position j ($n \leq j \leq L-n+1$ and $1 \leq n \leq M$) of a protein in the entire proteins as recovered in the step (8);

$D(j,n)=g(Z(j,n),Aj)$, and

(10) defining the representative value of the function of the j-th amino-acid residue in the amino acid sequence (length of L) as functional value Wj of the Z(j,n) and D(j,n);

$Wj=h(Z(j,1),Z(j,2), ..., Z(j,M),D(j,1),D(j,2), ..., D(j,M))$

(11) sequentially repeating the steps (3) to (10), to determine the individual Wj values of all the amino-acid residues at position $n \leq j \leq L-n+1$ in the amino acid sequence (length of L),

(12) selecting at least one amino-acid residue to be subjected to mutation on the basis of the alignment data carried out in the step (1) from the amino acid sequence (length of L) of the protein "A", and sequentially repeating the steps (3) to (10) for variant amino-acid residues in various mutated amino acid sequences where the selected amino-acid residue has been mutated into another amino-acid residue, to determine the Wj value of the variant amino-acid residue,

(13) selecting a mutated amino acid sequence wherein the Wj value of the variant amino-acid residue as determined in the step (12) is larger or smaller than the Wj value of the wild type amino-acid residue as determined in the step (10), and

(14) preparing a modified gene encoding the modified amino acid sequence from the protein "A" gene, and producing the modified protein as the expression product of the gene.

An eighth aspect of the present invention is a protein of which function is artificially modified by the methods for modifying the function of protein set forth above.

One embodiment of the function-modified protein is a thermophilic DNA polymerase, prepared by artificially modifying the amino acid sequence of Pfu DNA polymerase so that the elongation of synthesized DNA chain might not be terminated intermediately during the catalysis for the synthesis of a DNA chain complimentary to a single-stranded DNA, and more specifically, the thermophilic DNA polymerase is one comprising the amino acid sequence of SQ ID No.1. In association with this thermophilic DNA polymerase, the present application provides a DNA sequence encoding the amino acid sequence of SQ ID No.1 and a recombinant vector carrying the DNA sequence. Such recombinant vector includes recombinant plasmid pDP320 carried on *Escherichia coli* HMS174 (DE3) /pDP320 (FERM P-16052). Still furthermore, in accordance with the present invention, it is provided a method for preparing this thermophilic DNA polymerase, comprising culturing a cell transformed with an expression vector carrying the DNA sequence and isolating and purifying the objective enzyme generated in a culture medium.

Another embodiment of the function-modified protein is a thermophilic DNA polymerase, prepared by artificially modifying the amino acid sequence of Pfu DNA polymerase so that the synthesized DNA chain might be more elongated during the catalysis for the synthesis of a DNA chain complimentary to a single-stranded DNA, and more specifically, the thermophilic DNA polymerase is one comprising the amino acid sequence of SQ ID No.6 or a DNA polymerase comprising the amino acid sequence of SQ ID No.7. In association with this thermophilic DNA polymerase, the present application provides a DNA sequence encoding the amino acid sequence of SQ ID No.6 or 7, and a recombinant vectors carrying such DNA sequences, respectively. As such vectors, there are provided recombinant plasmid pDP5b17 carried on *Escherichia coli* HMS174 (DE3)/pDP5b17 (FERM BP-6189) (vector carrying the DNA sequence encoding the amino acid sequence of SQ ID No.1), and recombinant plasmid pDP5C4 carried on *Escherichia coli* HMS174 (DE3)/pDP5C4 (FERM BP-6190) (vector carrying the DNA sequence encoding the amino acid sequence of SQ ID No.1). Still furthermore, it is provided a method for producing the DNA polymerase, comprising culturing a cell transformed with an expression vector carrying the DNA sequence and isolating and purifying the objective enzyme produced in a culture medium.

The method for predicting a protein functional site in accordance with the first aspect of the present invention has been established on what will be described below. More specifically, protein is composed of a sequence of twenty amino acids, but the sequence is not random. Hence, the frequency of occurrence of a specific oligopeptide as a partial amino acid sequence in the entire proteins encoded by genome derived from an appropriate organism species is not constant, but some oligopeptides occur at high frequencies in various proteins while other oligopeptides rarely occur therein. It is recognized that among them, oligopeptides highly frequently occurring in common to various proteins do not have any potency to determine the uniqueness (specificity) of individual proteins, namely any potency to determine the functions, while oligopeptides occurring at low frequencies adversely determine the uniqueness and functions of individual proteins.

It is suggested that the functional site of protein is composed of oligopeptides occurring at low frequencies. Additionally, longer oligopeptides, more rarely occurring, increase in number. In other words, oligopeptide of length (n+1) as shown in the step (3) according to the method of the first aspect of the present invention is mostly the shortest oligopeptide occurring at a low frequency, and the calculated functional value Zj of amino-acid residue Aj at an appropriate position j in the oligopeptide is the coefficient of the occurrence (namely, the representative value of the function) of the amino-acid residue Aj at the position.

According to the method for predicting the protein functional site in accordance with the second aspect of the present invention, the contribution degree of the amino-acid residue Aj to the frequency of the occurrence of Aji-oligopeptide can be evaluated on the basis of the ratio Yji of the frequency of the occurrence of the Aji-oligopeptide to that of the Xji-oligopeptide as shown in the step (3), and thus, the calculated functional value Z (j, n) of the amino-acid residue Aj at an appropriate position of a protein serves as the coefficient of the occurrence of the amino-acid residue Aj at the position (namely, the representative value of the function).

Furthermore, the value Z(j, n) varies, depending on the species of amino-acid residue Aj. In the step (7) according to the inventive method, the distribution of the Z(j, n) value of each of twenty amino acids is determined in the entire proteins of organism "a", to determine D(j, n) value by normalizing the Z(j, n) value on the basis of the mean and standard deviation of Z(j,n) value of each amino acid, as determined on the basis of the distribution, which serves as the representative value of the function, after correction of the bias due to each amino-acid residue species.

Furthermore, longer oligopeptides, more rarely occurring, increase in number. Because the Z (j, n) and D(j, n) values generally vary, depending on the length (n), accordingly, the functional value Wj of the Z(j, n) and D(j, n) as determined on a variety of length (n) is defined as the representative value of the function.

The systems for predicting a protein functional site in accordance with the third and fourth aspects of the present invention are individually systems for automatically carrying out the methods in accordance with the first and second aspects of the present invention; the methods for modifying protein in accordance with the fifth and sixth aspects of the present invention are methods for preparing mutant proteins by substituting the amino-acid residue at the functional site predicted by the method of the first aspect of the present invention with another amino-acid residue. Still further, the method for modifying a protein in accordance with the seventh aspect of the present invention is a method for preparing a mutant protein by substituting the amino-acid residue at the functional site predicted by the method in accordance with the second aspect of the present invention with another amino-acid residue. In accordance with the eighth aspect of the present invention, a function-modified protein is provided. Furthermore, thermophilic DNA polymerase is provided as an embodiment of such protein.

The term "DNA polymerase" is the generic name of enzymes catalyzing the synthesis of a DNA chain complimentary to a single-stranded DNA. DNA polymerase is an essential enzyme for DNA sequencing and in vitro DNA amplification, and "thermophilic DNA polymerase" is inevitable for PCR (polymerase chain reaction) in terms of the automation of a series of the reaction cycles.

Such thermophilic DNA polymerase includes known ones, for example Taq, Pfu, KOD, which are separately used, depending on the characteristic performance. Pfu DNA polymerase in particular has been known as an enzyme with an extremely low frequency of erroneous reading during the synthesis of DNA strands (at a high fidelity). However, the Pfu DNA polymerase is inappropriate for the amplification of polymeric DNAs such as genome DNA, because the synthetic DNA yielded by the Pfu DNA polymerase is low and the activity thereof to elongate a synthetic chain is insufficient.

Thus, the present application provides a novel Pfu DNA polymerase prepared according to the method of the fifth aspect of the present invention.

BRIEF DESCRIPTION OF DRAWINGS

FIG. 17 depicts alignment charts of the amino acid sequences of the individual motif Cs of the α-type DNA polymerases Pfu (SEQ ID NO: 19), KOD (SEQ ID NO: 18) and MJ (SEQ ID NO: 17) derived from *Pyrococcus furiosus, Pyrococcus* sp. KOD, and *Methanococcus janaschii*, respectively;

BEST MODE FOR CARRYING OUT THE INVENTION

The method for predicting a functional site of a protein in accordance with the first aspect of the present invention is a method for predicting the functional site of an appropriate protein of organism "a" with a known genome data or cDNA analysis data, in the entire putative proteins of the organism "a", essentially comprising the following steps (1) to (6).

Step (1)

By determining the frequency of the occurrence of each amino acid and the frequencies of the occurrences of individual oligopeptides produced by permutations of twenty amino acids in the amino acid sequences of the entire proteins of the organism "a", the oligopeptide length (n) is determined.

The length n is determined, then, as the smallest integer satisfying the following criteria.

"Among oligopeptides of length n, the number of oligopeptides that occur once in the entire proteins is smaller than the number of oligopeptides that occur twice in the entire proteins; among oligopeptides of length (n+1), the number of oligopeptides that occur once in the entire proteins is larger than the number of oligopeptides that occur twice in the entire proteins."

Figure 1:
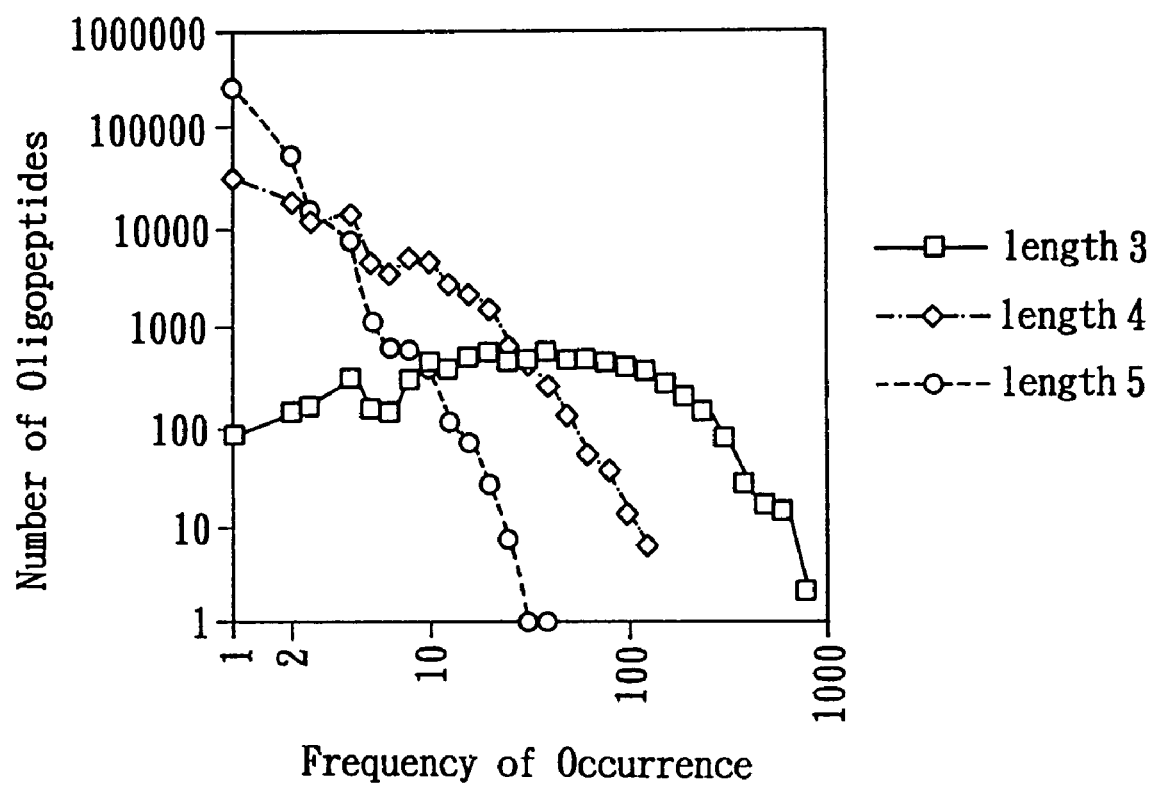
FIG. 1 depicts graphically the individual frequencies of the occurrences of oligopeptides of lengths 3, 4 and 5, and the distributions of the individual frequencies thereof according to the method of the first aspect of the present invention.

For example, FIG. 1 depicts distribution charts of the frequencies of the occurrences of oligopeptides of a length of 3, oligopeptides of a length of 4 and oligopeptides of a length of 5, in the entire proteins encoded by the genome of a microorganism *Methanococcus jannaschii* (Bult et al., Science 273, 1058-1073, 1996). In the case of the three types of length of the oligopeptides shown in FIG. 1, the smallest n in the step (1) is 3.

Step (2)

Given that the j-th amino-acid residue from the N-terminus of the amino acid sequence (length of L) of the protein as a subject for predicting a functional site is described here as Aj ($n+1 \leq j \leq L-n$), the frequency of occurrence of a partial sequence of the amino acid sequence of the protein, which sequence corresponds to the following Aji-oligopeptide of length (n+1), containing the j-th amino-acid residue Aj;

Aji-oligopeptide: aj1aj2 . . . Aji . . . ajnaj(n+1)
($1 \leq i \leq n+1$; Aj=Aji; and Aj is the i-th residue of the oligopeptide; and moreover, aj1=Aj−i+1, . . . , aj(n+1)=Aj−i+(n+1)), and the frequency of the occurrence of the following Xji-oligopeptide of length (n+1);

Xji-oligopeptide: aj1aj2 . . . Xji . . . ajnaj(n+1)
(the i-th residue Xji is any amino acid; and moreover, aj1=Aj−i+1, . . . , aj(n+1)=Aj−i+(n+1))

should be determined in the entire proteins of the organism "a".

Figure 2:
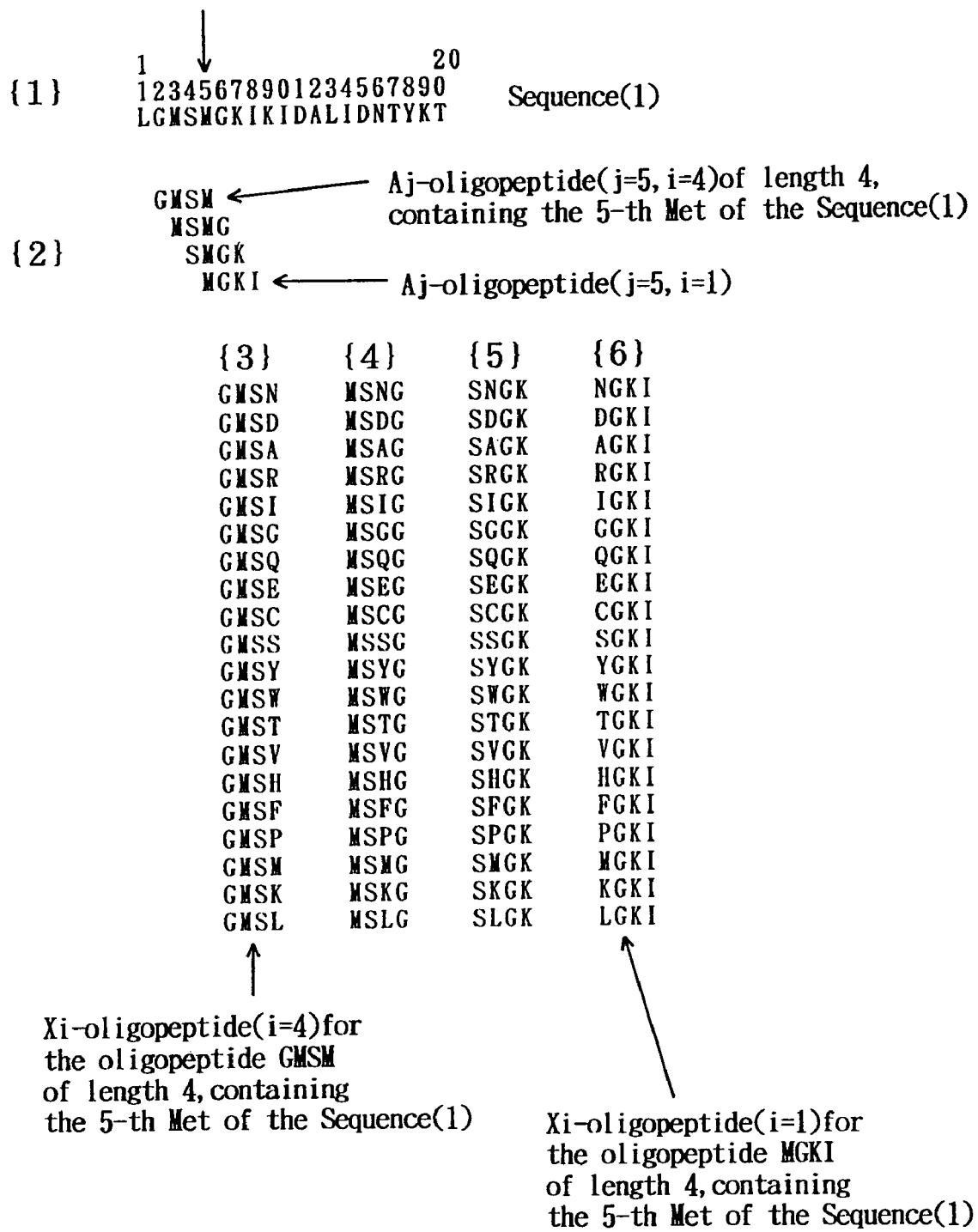
FIG. 2 depicts an example of an amino acid sequence of a length of 20, and examples of Aji-oligopeptide of a length of 4, containing the amino-acid residue Met at position 5 in the sequence and examples of Xji-oligopeptides [the sequence shown in part 1 corresponds to SEQ ID NO: 12, the sequences shown in part 2 correspond to SEQ ID NOs: 13-16 starting from the uppermost sequence, the column labeled 3 corresponds to SEQ ID NO: 13, column 4 corresponds to SEQ ID NO: 14, column 5 corresponds to SEQ ID NO: 15 and column 6 corresponds to SEQ ID NO: 16, GMSM given at the bottom of this figure corresponds to SEQ ID NO: 13 and MGKI at the bottom of the figure corresponds to SEQ ID NO: 16]

Such Aji-oligopeptide and Xji-oligopeptide can be illustrated for example in FIG. 2. The upper row (1) in FIG. 2 expresses in single letter code the partial sequence from the N-terminus to the 20-th amino-acid residue of the putative amino acid sequence on the basis of the gene MJ0885, which is believed to encode the α-type DNA polymerase of *Methanococcus jannaschii* (Bult et al., Science 273, 1058-1073, 1996); the middle row (2) expresses examples of Aji-oligopeptide of a length of 4, containing the 5-th amino-acid residue Met(M) in the amino acid sequence; and the rows (3) to (6) further below express examples of Xji-oligopeptide containing the 5-th amino-acid residue M.

Step (3)

Calculating ratio Yji of the frequency of the occurrence of the Aji-oligopeptide to that of the Xji-oligopeptide.

Step (4)

The mean Yj of the Yji is determined as follows.

$$Yj = \sum_{i=1}^{n+1} Yji/(n+1),$$

Step (5)

Monotonously decreasing functional value or monotonously increasing functional value Zj of Yj is determined as follows;

$Zj=f(Yj)$.

The Zj value is defined as the representative value of the function of the j-th amino-acid residue of the amino acid sequence (length of L).

Step (6)

By subsequently repeating the steps (2) to (5) sequentially and determining the Zj value of each of all the amino-acid residues at position $n+1 \leq j \leq L-n$, the degree of the involvement of each amino-acid residue in the function of the protein is predicted by using the dimension of the Zj value as an indicator. More specifically, because the manner of occurring of each amino-acid residue in the context is expressed as the functional value Zj of Yj, a larger Zj value indicates a lower frequency of occurrence of the amino-acid residue if Zj is a monotonously decreasing functional value, which suggests that the amino-acid residue has higher responsibility over the fulfillment of the function. If Zj is a monotonously increasing function, additionally, it is suggested that an amino-acid residue with a smaller Zj value has greater responsibility over the function.

By expressing the Zj value of each amino-acid residue for example in a distribution chart wherein the Zj value is plotted on the vertical axis while the amino acid sequence is shown on the horizontal axis, furthermore, the functional site can be confirmed at a glance, which is preferable as an embodiment for carrying out the present invention.

The method for predicting a protein functional site in accordance with the second aspect of the present invention is a method for predicting a functional site of an appropriate protein in the entire putative proteins of the organism "a" with a known genome data or cDNA analysis data, essentially comprising the following steps (1) to (9).

Step (1)

The frequency of the occurrence of each amino acid and the frequencies of the occurrences of individual oligopeptides produced by permutations of twenty amino acids, in the amino acid sequences of the entire proteins of the organism "a", are determined.

Figure 3:
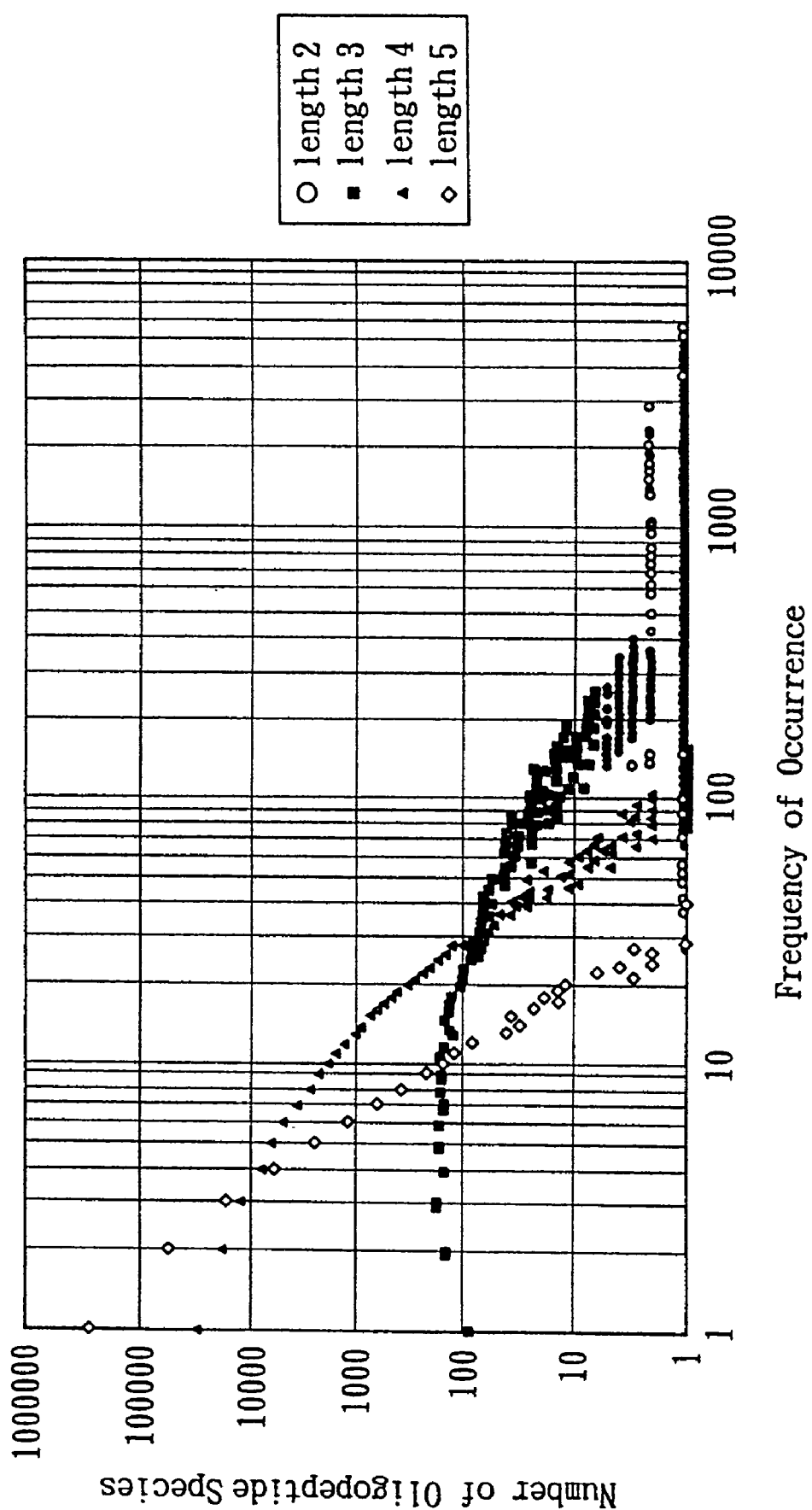
FIG. 3 depicts graphically the individual frequencies of the occurrences of oligopeptides of lengths of 2, 3, 4 and 5, and the distributions of the individual frequencies thereof according to the method of the second aspect of the present invention.

For example, FIG. 3 shows a distribution chart of the frequencies of the occurrences of oligopeptides of a length of 3, oligopeptides of a length of 4 and oligopeptides of a length of 5, which are determined in the entire proteins encoded by the genome of a microorganism *Methanococcus jannaschii* (Bult et al., Science 273, 1058-1073, 1996) on the basis of the genome data of the microorganism.

Figure 4:
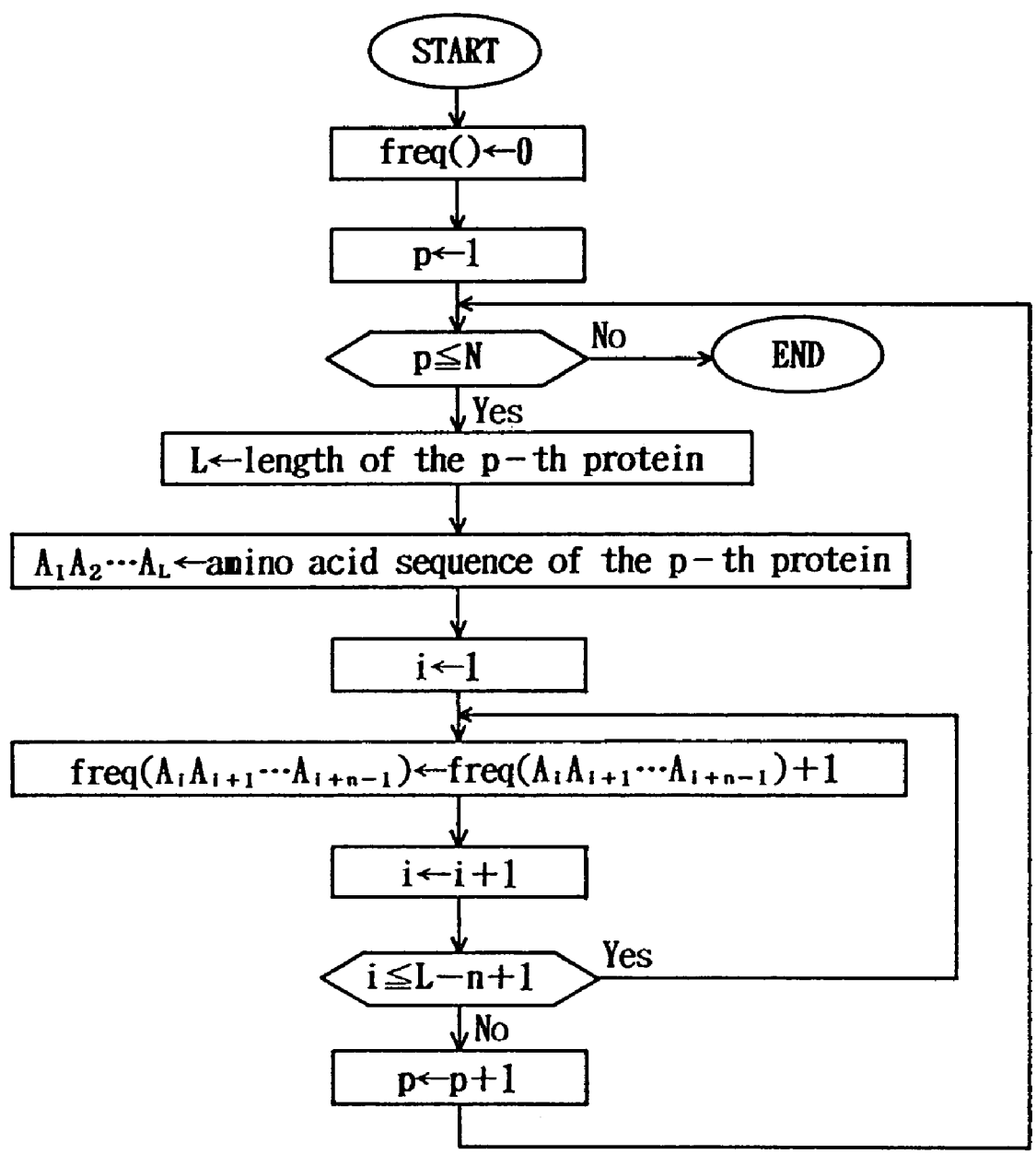
FIG. 4 depicts an example of the flow chart for conducting the step (1) of the method of the second aspect of the present invention.

FIG. 4 depicts an example of the flow chart for carrying out the step (1).

Step (2)

As to an appropriate protein of organism "a",

Step (2')

Given that the j-th amino-acid residue from the N-terminus of the amino acid sequence (length of L) of the protein is described here as Aj, the frequency of the occurrence of a partial sequence of the amino acid sequence of the protein, which sequence corresponds to the following Aji-oligopeptide of an appropriate length n ($1 \leq n \leq M$, provided that "M" is the smallest length of oligopeptides satisfying the following criterion; all the oligopeptides of length M are at frequency 1 of the occurrence), containing the j-th amino-acid residue Aj ($n \leq j \leq L-n+1$);

Aji-oligopeptide: aj1aj2 . . . Aji . . . ajn
($1 \leq i \leq n$; Aj=Aji and Aji is the i-th residue of the oligopeptide; and moreover, aj1=Aj−i+1, . . . , aj(n+1)=Aj−i+(n+1)), and the frequency of the occurrence of the following Xji-oligopeptide of the length n corresponding to the length of the Aji-oligopeptide;

Xji-oligopeptide: aj1aj2 ... Xji ... ajn
(the i-th residue Xji is any amino acid; and moreover, aj1=Aj−i+1, ..., aj(n+1)=Aj−i+(n+1)), are determined in the entire proteins of the organism "a".

In the same manner as by the method of the first aspect of the present invention, such Aji-oligopeptide and Xji-oligopeptide are for example illustrated as in FIG. 2.

Step (3)

The ratio Yji of the frequency of the occurrence of the Aji-oligopeptide to that of the Xji-oligopeptide is determined.

Figure 5:
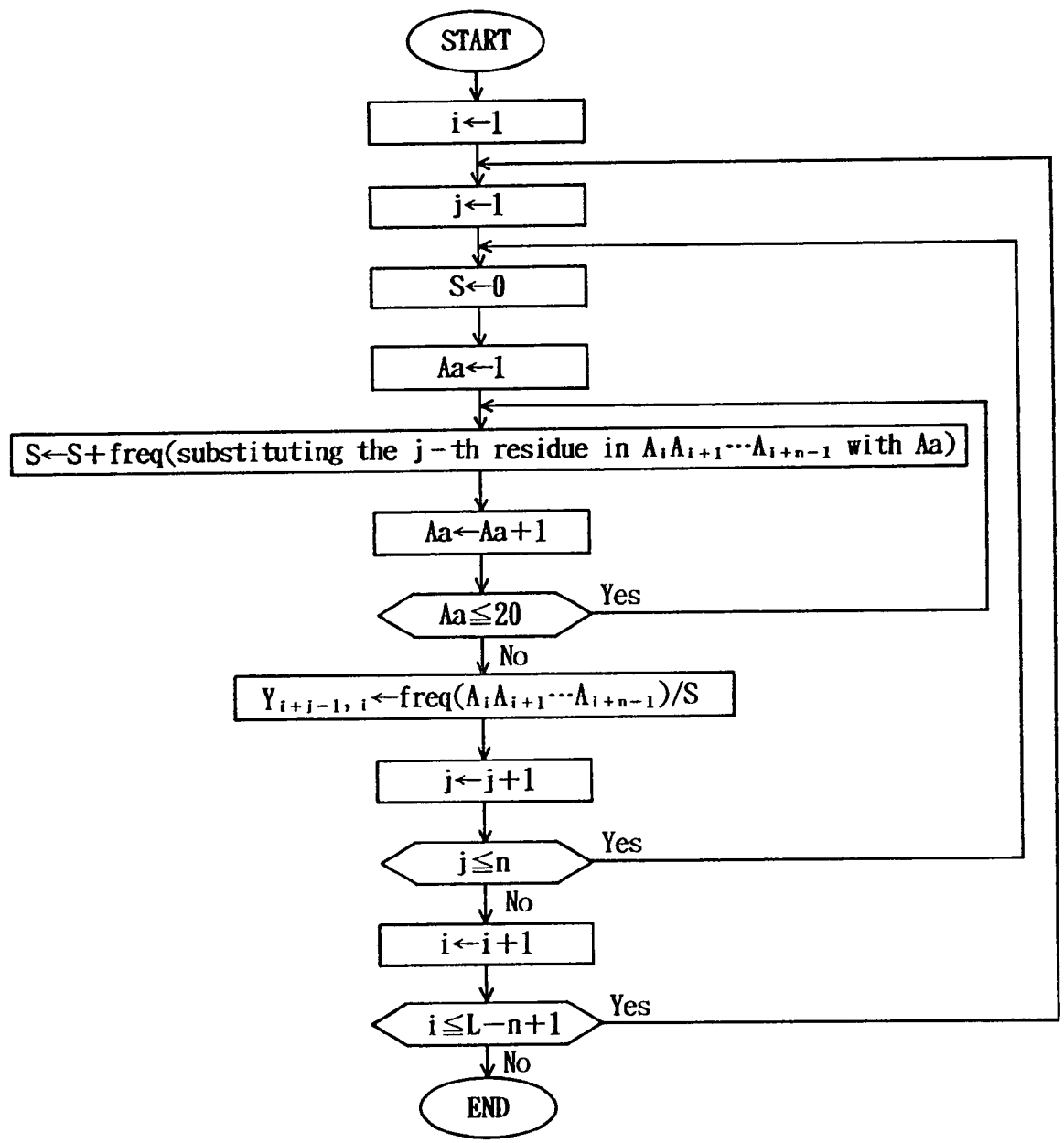
FIG. 5 depicts an example of the flow chart for conducting the steps (2') to (3) of the method of the second aspect of the present invention.

FIG. 5 depicts an example of the flow chart for carrying out the aforementioned steps (2') to (3).

Step (4)

The mean Y(j, n) of the Yji is determined as described below.

$$Y(j,n) = \sum_{i=1}^{n} Yji/n.$$

Step (5)

The logarithmic value Z(j, n) of Y(j, n) is determined as follows.

$Z(j,n)=-\log(Y(j,n))$

Figure 6:
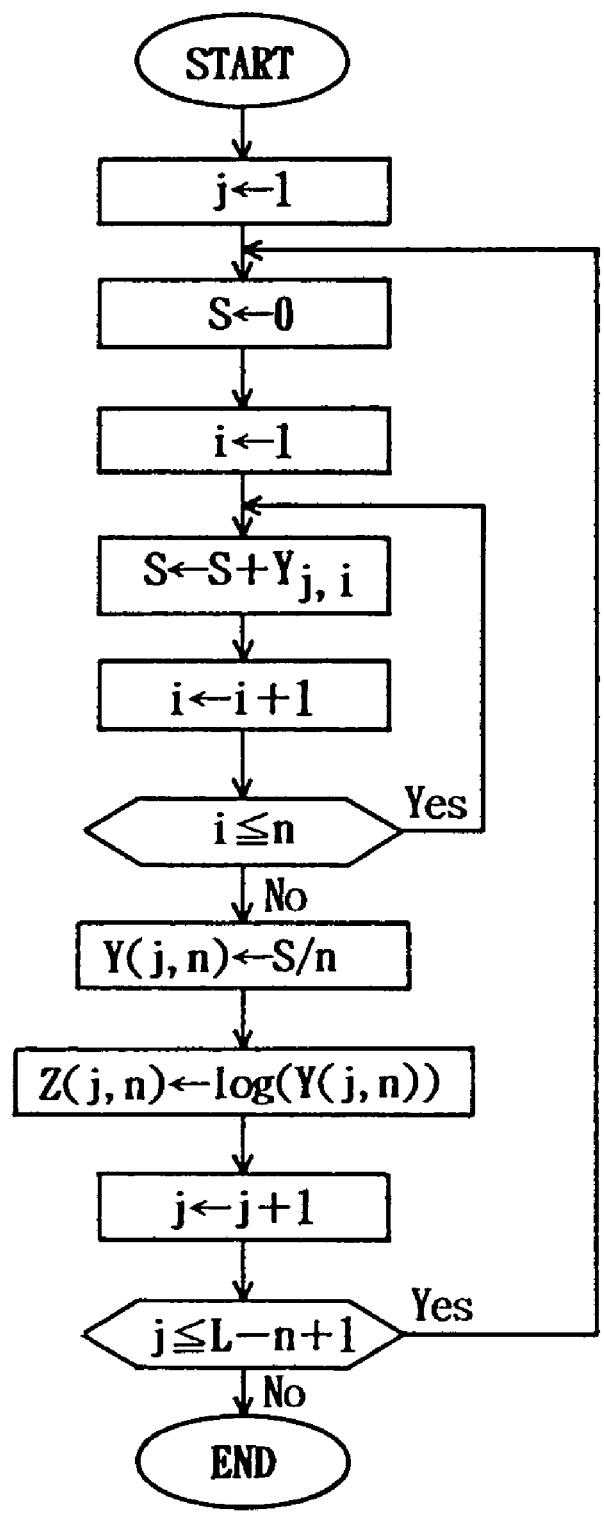
FIG. 6 depicts an example of the flow chart for conducting the steps (4) to (5) of the method of the second aspect of the present invention.

FIG. 6 depicts an example of the flow chart for carrying out the aforementioned steps (4) to (5).

Step (6)

By subsequently repeating the steps (2') to (5) sequentially, the Z(j, n) value of each of all the amino-acid residues at position $n \leq j \leq L-n+1$ in the amino acid sequence (length of L) is determined.

Step (7)

By sequentially repeating the steps (2) to (6) over the entire proteins of the organism "a", thereby determining the distribution of the Z(j,n) value of each amino-acid residue in the entire proteins, and the Z(j,n) values are classified into twenty according to the twenty amino acids, and then determining mean Av(Aa) of the Z(j,n) values for each amino acid Aa and the standard deviation Sd (Aa) of the distribution thereof, on the basis of the distribution, to determine function g to the j-th amino-acid residue Aj of a protein for normalizing the difference in distribution due to (or among?) the species of amino-acid residues is determined;

$g=g(Z(j,n),Aj)=[Z(j,n)-Ad(Aa]/Sd(Aa)$ (provided that Aj=Aa; and $1 \leq n \leq M$).

Figure 7:
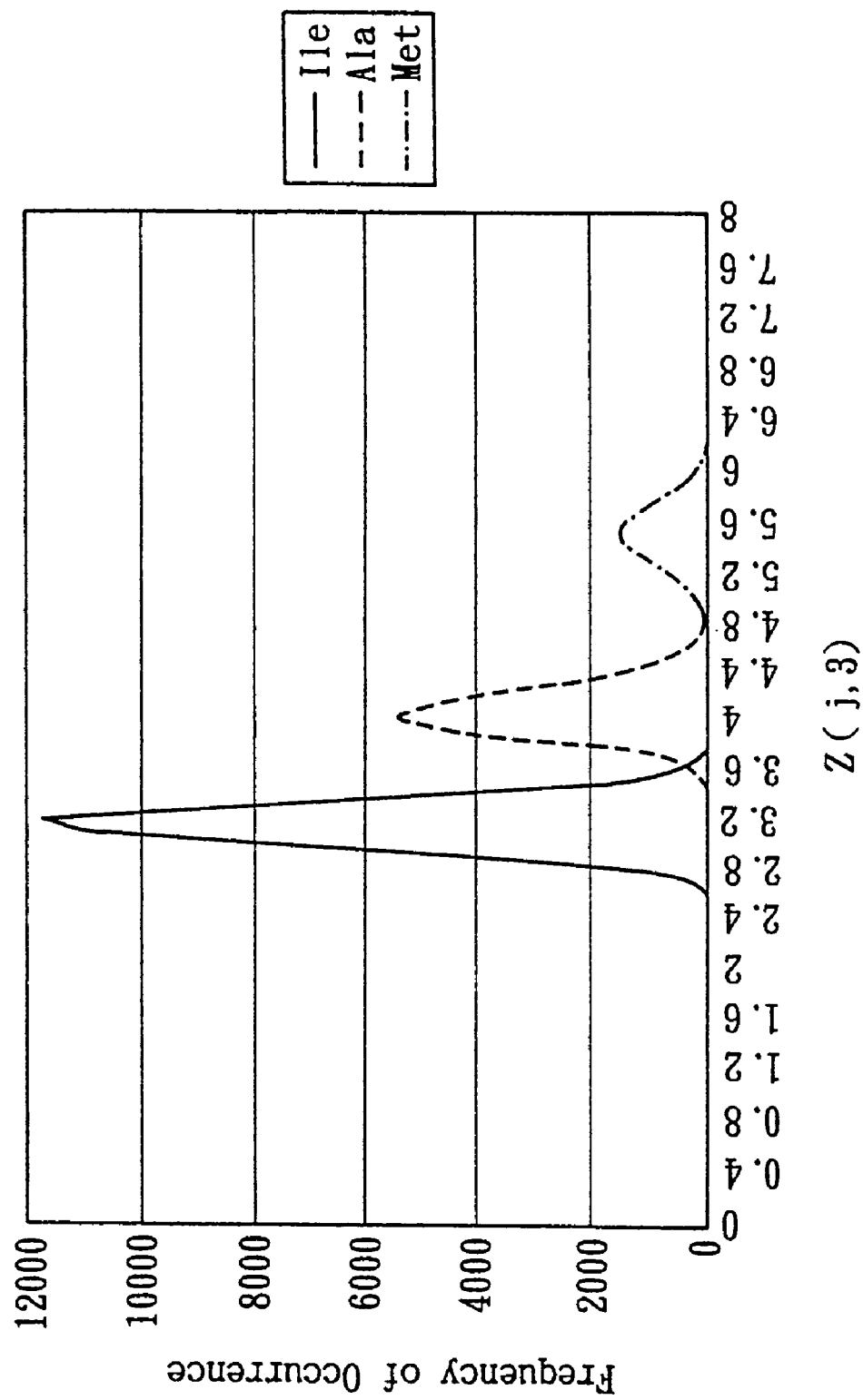
FIG. 7 depicts a distribution of the frequency of $Z(j, 3)$ of each of three amino acids, see below, according to the method of the second aspect of the present invention, wherein the solid line expresses the distribution of that of isoleucine (Ile); the dotted line expresses the distribution of that of alanine (Ala); and the alternate long and short dash line expresses the distribution of that of methionine (Met)

For example, FIG. 7 depicts a distribution of the frequency of Z (j, n) for three species of amino acids, namely isoleucine (Ile), alanine (Ala) and methionine (Met), in the entire proteins encoded by the genome of *Methanococcus jannaschii* (Bult et al., Science 273, 1058-1073, 1996). Based on the distribution, the mean and standard deviation of the Z(j, n) values for an amino acid isoleucine (Ile), namely Ad (Ile) and Sd(Ile), respectively, are determined as Ad(Ile)=3.16 and Sd(Ile)=0.17, and the function g for Aj=Ile is determined as follows.

$g=g(Z(j,n),Aj)=(Z(j,n)-3.16)/0.17$

Figure 8:
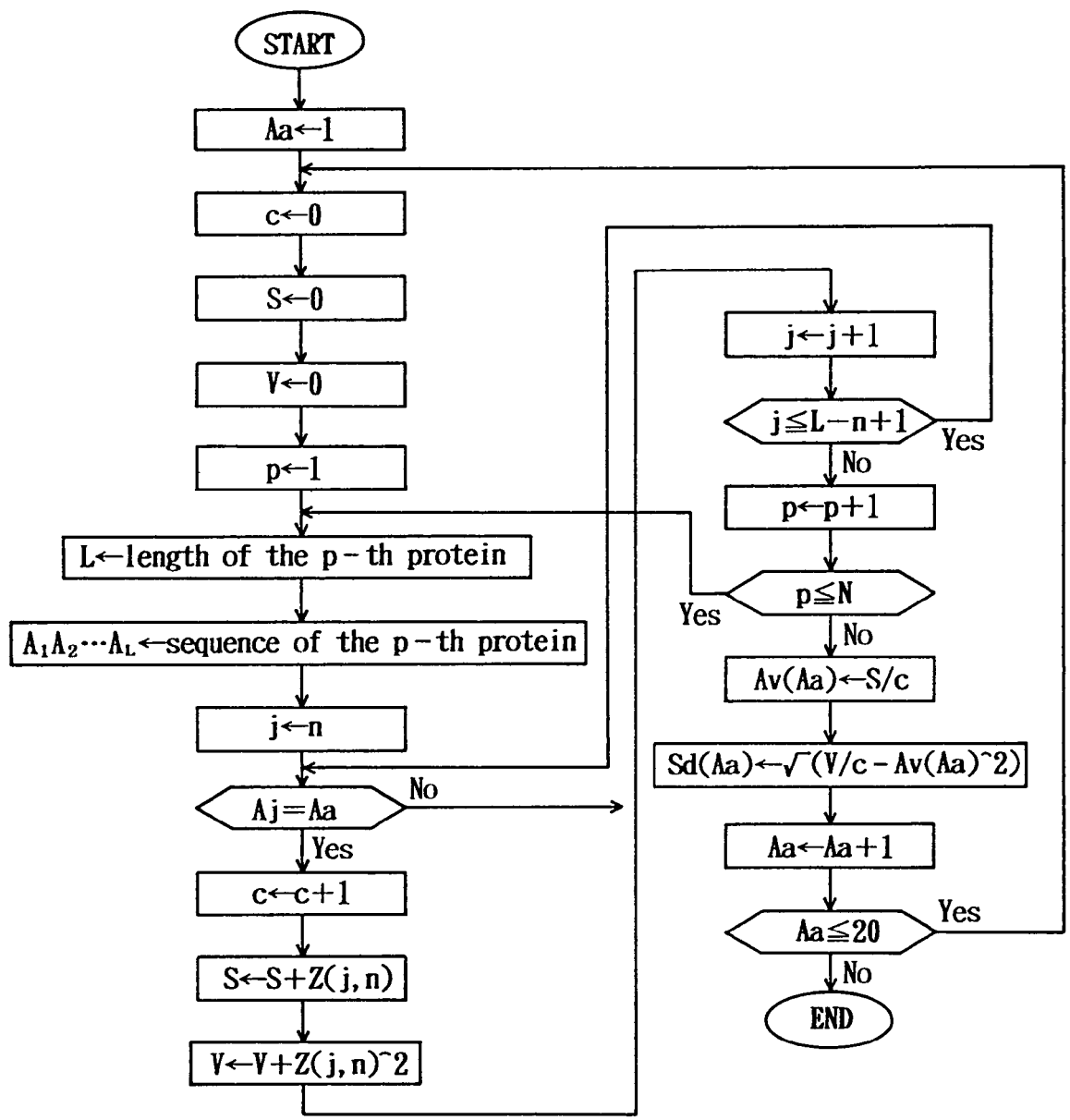
FIG. 8 depicts an example of the flow chart for conducting the step (7) of the method of the second aspect of the present invention.

FIG. 8 depicts an example of the flow chart for carrying out the step (7).

Step (8)

The value D(j, n) of the function g of each of all the amino-acid residues Aj at position $n \leq j \leq L-n+1$ in the amino acid sequence (length of L) as recovered in the step (7) is determined;

$D(j,n)=g(Z(j,n),Aj)$.

Figure 9:
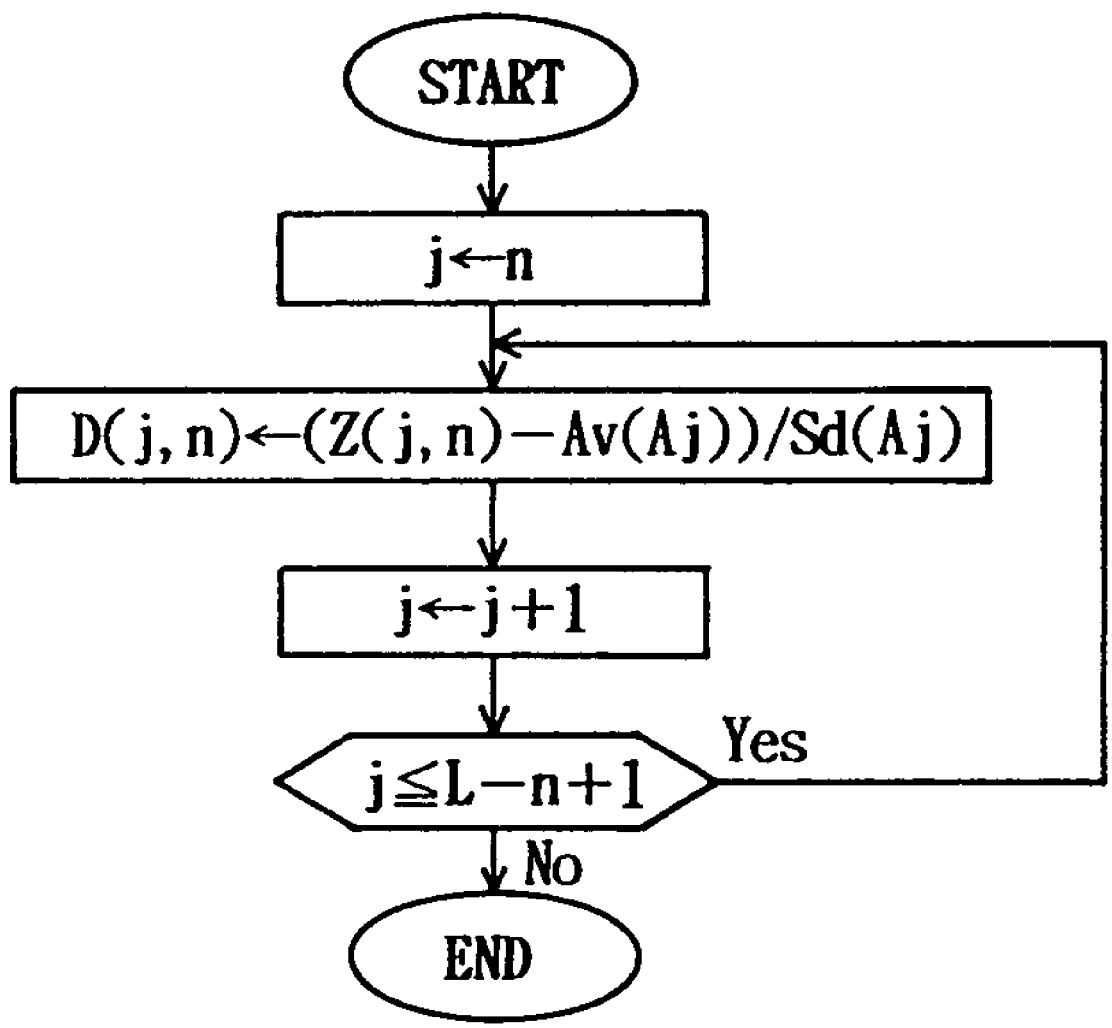
FIG. 9 depicts an example of the flow chart for conducting the step (8) of the method of the second aspect of the present invention.

FIG. 9 depicts an example of the flow chart for carrying out the step (8).

Step (9)

The functional value Wj of the Z (j, n) value and the D (j, n) value is determined as follows.

$Wj=h(Z(j,1), Z(j,2), ..., Z(j,M), D(j,1), D(j,2), ..., D(j,M))$

By defining the value of the Wj as the representative value of the function of the j-th amino-acid residue in the amino acid sequence (length of L), the degree of the responsibility of each amino-acid residue over the function of the protein is estimated by using the dimension of the Wj value as an indicator.

Figure 10:
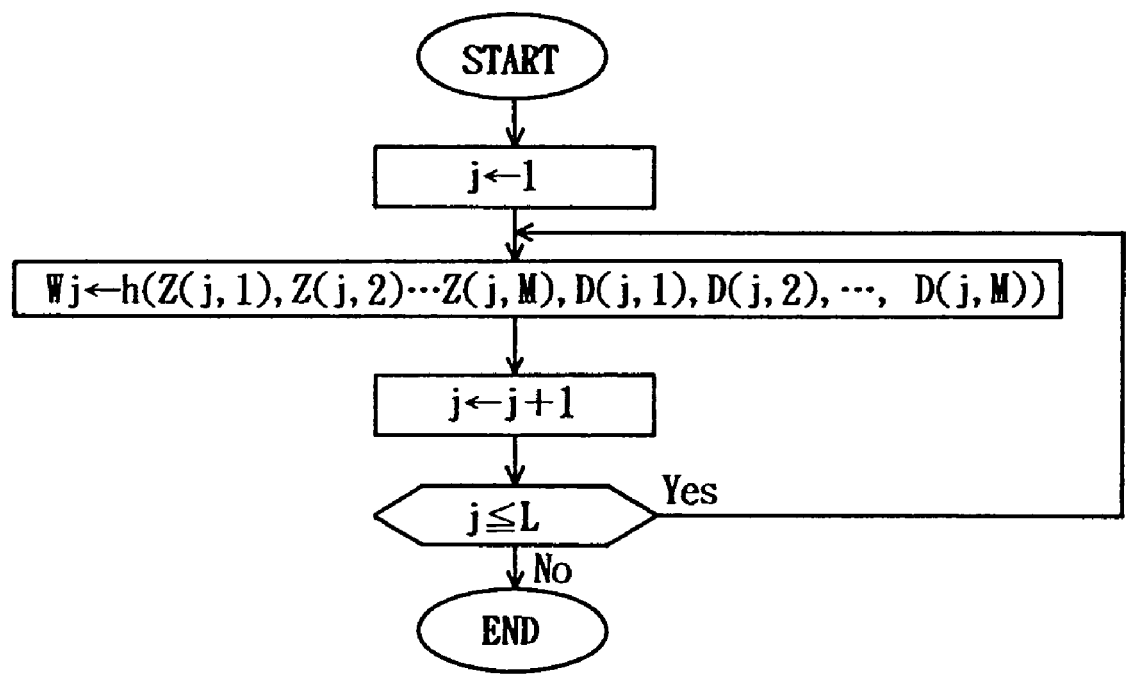
FIG. 10 depicts an example of the flow chart for conducting the step (9) of the method of the second aspect of the present invention.

FIG. 10 depicts an example of the flow chart for carrying out the step (9).

By expressing the Wj value of each amino-acid residue for example in a distribution chart wherein the Wj value is plotted on the vertical axis while the amino acid sequence is shown on the horizontal axis, furthermore, the functional site can be confirmed at a glance, which is preferable as an embodiment for carrying out the present invention.

If the three-dimensional structure of the protein as a subject for predicting the functional site is known or if a three-dimensional structure model thereof can be prepared by known methods (for example, homology modeling method, Peitsch, Proceedings of the Fifth International Conference on Intelligent Systems for Molecular Biology, 1997, 5, 234-236), the distribution is expressed on the three-dimensional structure, whereby a spatial arrangement of an amino-acid residue as a candidate of a novel functional site can be confirmed, which is preferable as an embodiment for carrying out the invention.

Figure 11:
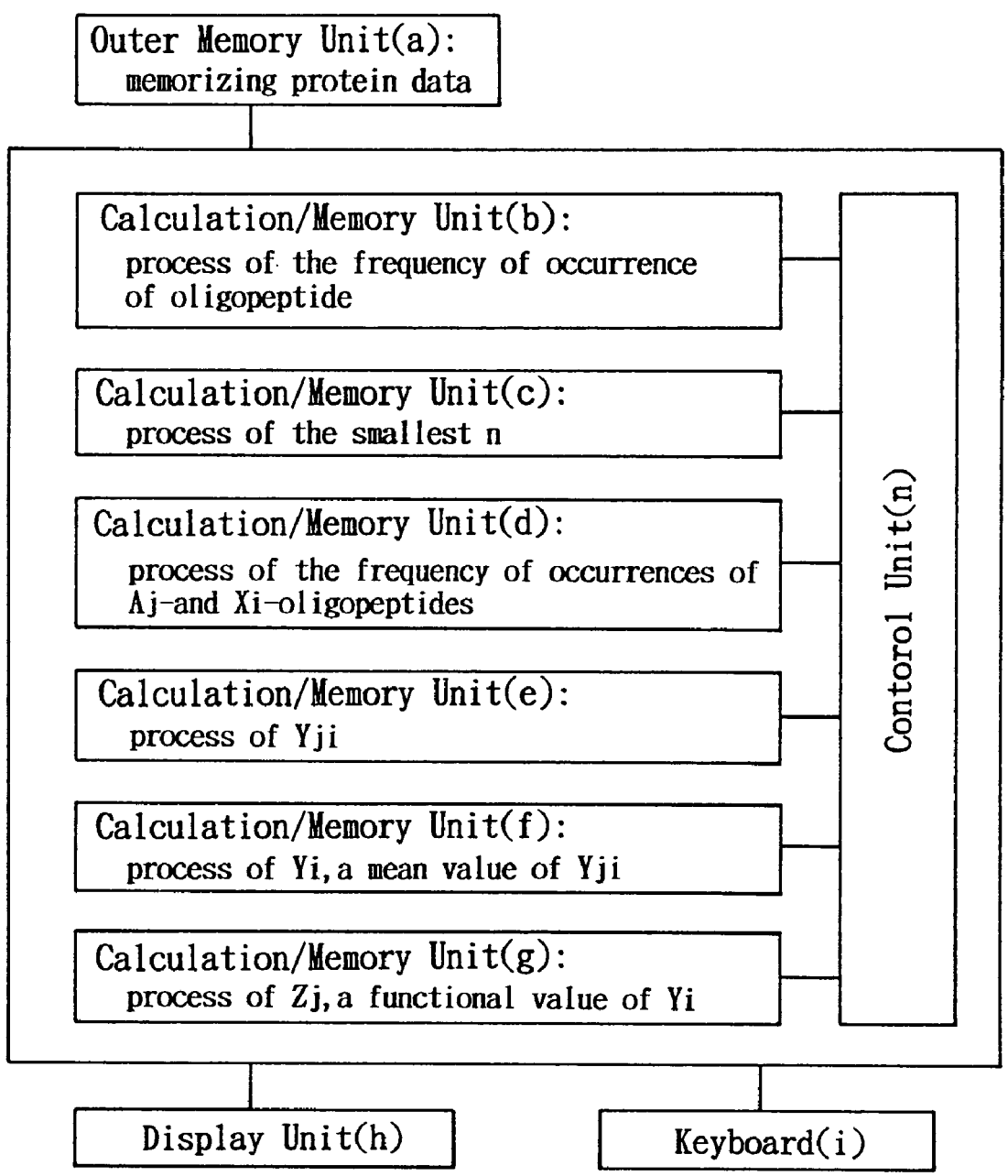
FIG. 11 depicts a block diagram illustrating the system of the third aspect of the present invention.

The system for predicting a functional site of a protein in accordance with the third aspect of the present invention is a system for automatically carrying out the method for predicting a functional site in accordance with the first aspect of the present invention, at least comprising the following units (a) to (g) for conducting the steps (1) to (6) according to the method of the first aspect of the present invention, as shown for example in the composition example in FIG. 11.

Outer Memory Unit (a):

Unit memorizing the amino acid sequence data of a protein or an existing protein data base for use in the step (1).

Calculation/Memory Unit (b):

Unit, composed of CPU calculating the frequencies of the occurrences of individual oligopeptides as determined in the step (1), and a memory unit having the memory of the calculation results.

Calculation/Memory Unit (c):

Unit, composed of CPU calculating the smallest length (n) of oligopeptides as determined in the step (1) and a memory unit having the memory of the length n.

Calculation/Memory Unit (d):

Unit, composed of CPU calculating the frequencies of occurrence of each amino acid and the frequencies of occurrence of Aji-oligopeptide and Xji-oligopeptide in the entire proteins as determined in the step (2) and a memory unit having the memory of the calculation results.

Calculation/Memory Unit (e):
Unit, composed of CPU calculating the Yji value as determined in the step (3) and a memory unit having the memory of the Yji value.

Calculation/Memory Unit (f):
Unit, composed of CPU calculating the Yj value as determined in the step (4) and a memory unit having the memory of the Yj value.

Calculation/Memory Unit (g):
Unit, composed of CPU calculating the Zj value as determined in the step (5) and a memory unit having the memory of Zj.

Additionally, the system for predicting a functional site is provided with the following display unit (h) in a preferable embodiment.

Display Unit (h):
Unit displaying the Zj value of each amino-acid residue recovered in the calculation/memory unit (g) in a distribution chart.

The system of the present invention may be equipped with keyboard (i) and control unit (j) and the like as illustrated in FIG. 11, in addition to these units (a) to (h).

Figure 12:
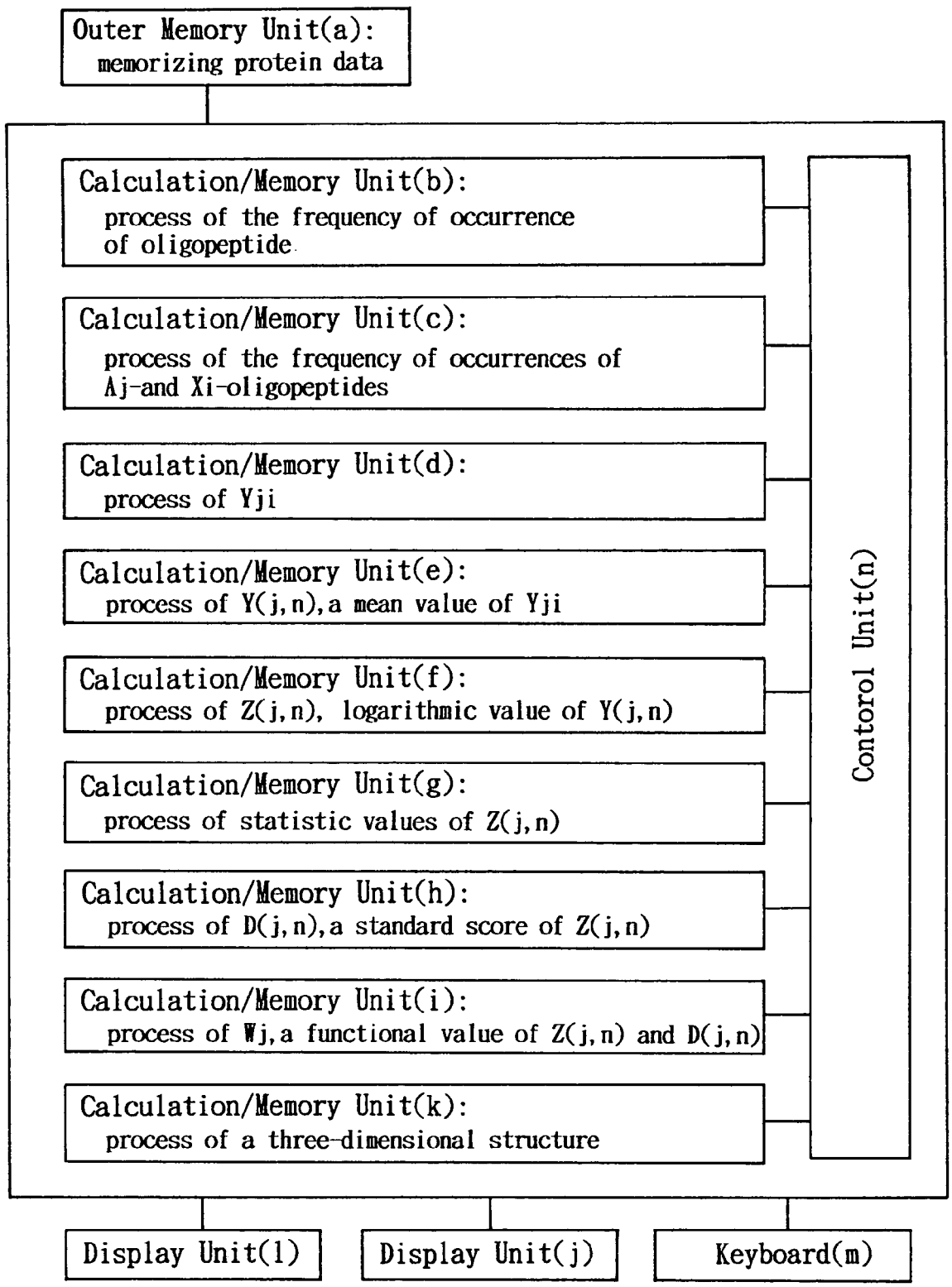
FIG. 12 depicts a block diagram illustrating the system of the fourth aspect of the present invention.

According to the fourth aspect of the present invention, the system for predicting a protein functional site is a system for automatically conducting the method of the second aspect of the present invention, at least comprising the following units (a) to (i) for carrying out the steps (1) to (9) according to the method of the second aspect of the present invention, as shown in the composition example in FIG. 12.

Outer Memory Unit (a):
Unit memorizing the amino acid sequence data and an existing protein data base for use in the step (1).

Calculation/Memory Unit (b):
Unit, composed of CPU calculating the frequencies of the occurrences of individual oligopeptides as determined in the step (1) and a memory unit having the memory of the calculation results.

Calculation/Memory Unit (c):
Unit, composed of CPU calculating the frequencies of occurrence of each amino acid and the individual frequencies of the occurrences of Aji-oligopeptide and Xji-oligopeptide in the entire proteins as determined in the step (2') and a memory unit having the memory of the calculation results.

Calculation/Memory Unit (d):
Unit, composed of CPU calculating Yji as determined in the step (3) and a memory unit having the memory of the Yji value.

Calculation/Memory Unit (e):
Unit, composed of CPU calculating the Y(j, n) value as determined in the step (4) and a memory unit having the memory of the Y(j, n) value.

Calculation/Memory Unit (f):
Unit, composed of CPU calculating the Z(j, n) value as determined in the steps (5) and (6) and a memory unit having the memory of the Z(j, n) value.

Calculation/Memory Unit (g):
Unit, composed of CPU calculating the g value as determined in the step (7) and a memory unit having the memory of the g value.

Calculation/Memory Unit (h):
Unit, composed of CPU calculating the D(j, n) value as determined in the step (8) and a memory unit having the memory of the D(j, n) value.

Calculation/Memory Unit (i):
Unit, composed of CPU calculating the Wj value as determined in the step (9) and a memory unit having the memory of the Wj value.

Additionally, the system for predicting a functional site in accordance with the fourth aspect of the present invention may be equipped with an appropriate combination of the following units (j) to (l).

Display Unit (j):
Unit displaying the Wj value of each amino-acid residue as recovered with the unit (i) in a distribution chart.

Calculation/Memory Unit (k):
Unit memorizing an existing database of protein three-dimensional structures or unit preparing a three-dimensional structure model based on an amino acid sequence according to a known method and memorizing the three-dimensional structure.

Display Unit (l):
Unit displaying the Wj value of each amino-acid residue in a distribution chart on the three-dimensional structure stored in the database or three-dimensional structure model recorded on the unit (k).

The system of the present invention may satisfactorily be equipped with keyboard (m) and control unit (n) and the like as illustrated in FIG. 12, in addition to these units (a) to (l).

The method for modifying the function of a protein in accordance with the fifth aspect of the present invention will be described below. The method is a method for modifying the function of protein "A", which function has been known, derived from the entire putative proteins of organism "a" with a known genome data or cDNA analysis data, essentially comprising the following steps (1) to (10).

Step (1):
Extracting proteins closely related to the protein "A" from an existing protein data base and subjecting the proteins to alignment.

Steps (2) to (7):
Subjecting the amino acid sequences of the entire proteins of the organism "a" to the steps (1) to (6) according to the method of the first aspect of the present invention.

Step (8):
Selecting at least one amino-acid residue to be subjected to mutation from the amino acid sequence (length of L) of the protein "A" on the basis of the alignment data recovered in the step (1), sequentially repeating the steps (3) to (6) for a variant amino-acid residue of various mutated amino acid sequences where the selected amino-acid residue has been mutated into another amino-acid residue, to determine the Zj value of the variant amino-acid residue.

Step (9):
Selecting a mutated amino acid sequence wherein the Zj value of the variant amino-acid residue as determined in the step (8) is larger or smaller than the Zj value of the intact amino-acid residue as determined in the step (7).

Step (10):

Preparing a modified gene of the protein "A", which gene encodes the mutant amino acid sequence selected in the step (9), and expressing the modified gene in an appropriate host-vector system to prepare modified protein "A".

In accordance with the sixth aspect of the present invention, the method for modifying a protein function is a method for modifying the function of protein "B" derived from organism "b" with an unknown genome data or cDNA analysis data, essentially comprising the following steps (1) to (10).

Step (1):

Extracting protein "A" most closely related to protein "B" from the entire putative proteins of organism "a" with a known genome data or cDNA analysis data and subjecting the protein "A" to alignment, or extracting proteins closely related to protein "B" from an existing protein data base to subject the proteins to alignment.

Steps (2) to (8):

Conducting the steps (2) to (8) of the method of the third aspect of the present invention over the amino acid sequences of the entire proteins of the organism "a".

Step (9):

Selecting a position that should be mutated and an amino acid residue for which should be substituted wherein the Zj value of the substituted amino-acid residue as determined in the step (8) is larger or smaller than the Zj value of the intact amino-acid residue as determined in the step (7).

Step (10):

Preparing a modified gene of the protein B according to a known method, which gene encodes the amino acid sequence mutated at the position to another amino acid residue as selected in the step (9), and expressing the modified gene in an appropriate host-vector system to prepare modified protein B.

As has been described above, the methods for modifying the protein function in the fifth and sixth aspects of the present invention, comprising the method for predicting a functional site of the first aspect of the present invention, are characterized in that an unknown functional site of protein is newly found and is subjected to mutation.

Furthermore, the method for modifying a protein function according to the seventh aspect of the present invention also utilizes the method for predicting the function in accordance with the second aspect of the present invention, whereby the method can be carried out in the same manner as in the case of the fifth aspect of the present invention.

Figure 13:
FIG. 13 depicts the electrophoresis results of conventional Pfu DNA polymerase and KOD DNA polymerase, indicating the primer elongating activities thereof.

The eighth aspect of the present invention is a protein of which function is artificially modified by the method of the fifth to seventh aspect of the present invention. An embodiment of such protein is thermophilic DNA polymerase, which is more specifically an enzyme prepared by modifying, in accordance with the sixth aspect of the present invention, a thermophilic Pfu DNA polymerase derived from *Pyrococcus furiosus* in a genetic engineering manner by the known method for preparing mutant gene (Strategies, Vol. 9, p. 3-4, 1996) (the thermophilic DNA polymerase of the present invention is sometimes referred to as "modified Pfu DNA polymerase"). The enzyme can be prepared as follows. More specifically, because the nucleotide sequence of the gene of Pfu DNA polymerase is known (Nucleic Acids Research, Vol. 21, p. 259-265, 1993), the gene of Pfu DNA polymerase is prepared by PCR comprising synthetically preparing an oligopeptide complementary to both the ends by using the genome DNA of the archaebacterium as template and using the oligopeptide as primer. The DNA fragment of the gene is cloned into a vector, and the gene is subsequently subjected to mutation by the method described in the reference mentioned above. In accordance with the present invention, in particular, the mutation of the gene was executed by nucleotide substitution, so that a part of the amino acid sequence of Pfu DNA polymerase might be substituted with the amino-acid residues from KOD DNA polymerase. In terms of amino acid sequence, Pfu DNA polymerase has about 80% homology with KOD DNA polymerase, and therefore, similar synthetic termination occurs during PCR (FIG. 13), but the elongation rate with KOD DNA polymerase is about 6-fold the rate with Pfu DNA polymerase. By substituting some amino-acid residues of Pfu DNA polymerase with some amino-acid residues of KOD DNA polymerase, the synthetic termination of the chain elongation might be improved or the elongation rate turns rapid, which possibly enables the recovery of an enzyme capable of elongating a DNA chain under way of synthesis more longer. By expressing in *Escherichia coli* the mutant gene that was mutated in such a manner and recovering and purifying the expression product, the modified Pfu DNA polymerase of the present invention was recovered.

The thermophilic DNA polymerase (modified Pfu DNA polymerase I) of the present invention is more specifically an enzyme of the amino acid sequence of SQ ID No.1. The amino acid sequence is a novel sequence prepared by identifying potentially function-modifiable amino-acid residues of the amino acid sequence of the conventionally known Pfu DNA polymerase, according to the inventive method for predicting a functional site, and substituting the amino-acid residues as shown in Table 1. By using the novel enzyme then for DNA synthesis by PCR, for example, the synthetic termination occurring when using the conventional DNA polymerases is almost totally overcome, as shown in the following examples. It is needless to say that template DNA chains to be highly efficiently amplified with the conventional polymerase can be amplified at high efficiency in the same manner.

Furthermore, the thermophilic DNA polymerases (modified Pfu DNA polymerases II and III) of the present invention are more specifically enzymes of amino acid sequences of SQ ID Nos. 6 and 7, which are novel sequences prepared by identifying potentially function-modifiable amino-acid residues of the amino acid sequence of the Pfu DNA polymerase, according to the inventive method for predicting a functional site, and substituting the amino-acid residues as shown in Table 1. By using the novel enzymes then for DNA synthesis by PCR, for example, synthetic polymeric products can be recovered at large scales, as shown in the following examples.

TABLE 1

| Modified DNA polymerases | Positions | Wild-type amino acid | Modified amino acid |
|---|---|---|---|
| I | 2 | Ile | Val |
|  | 533 | Phe | Tyr |
|  | 538 | Leu | Ile |
|  | 540 | Ile | Ser |
|  | 545 | Leu | Phe |
|  | 546 | Tyr | Phe |
| II | 2 | Ile | Val |
|  | 710 | Pro | Arg |
|  | 712 | Ser | Arg |
|  | 713 | Asn | Asp |
|  | 717 | Leu | Pro |
| III | 2 | Ile | Val |
|  | 717 | Leu | Pro |

The DNA sequences encoding these modified Pfu DNA polymerases include for example the mutant genes of the Pfu DNA polymerase gene, as recovered during the process of enzyme preparation. As to these mutant genes, the DNA sequences encoding the amino acid sequences of SQ ID Nos.1, 6 and 7 for example have been cloned in recombinant plasmids p320, pDP5b17 and pDP5C4, respectively, and these recombinant plasmids have been integrated in *Escherichia coli* HMS174 (DE3) and deposited at the Life Engineering and Industrial Technology Research Institute, the Agency of Industrial Science and Technology, Japan (Accession Nos. FERM P-16052, FERM BP-6189 and FERM BP-6190, respectively).

Additionally, the DNA sequences of the present invention may appropriately be designed as DNA sequences with conjugated nucleotide codons corresponding to the individual amino-acid residues of SQ ID No.1, 6 or 7.

The thermophilic DNA polymerases of the present invention may be expressed in microorganisms such as *Escherichia coli*, which may thereafter be recovered. By inserting and integrating the DNA sequence into an expression vector with an origin of replication in a microorganism, a promoter, a ribosome-binding site, a cDNA cloning site, and a terminator and the like to prepare an expression vector, transforming a host cell with the expression vector and thereafter culturing the resulting transformant, an enzyme encoded by the DNA sequence can be generated in the microorganism at a large scale.

EXAMPLES

The present invention will now be described more specifically in more detail with reference to examples, but the invention is not limited to the following examples.

Example 1

Figure 14:
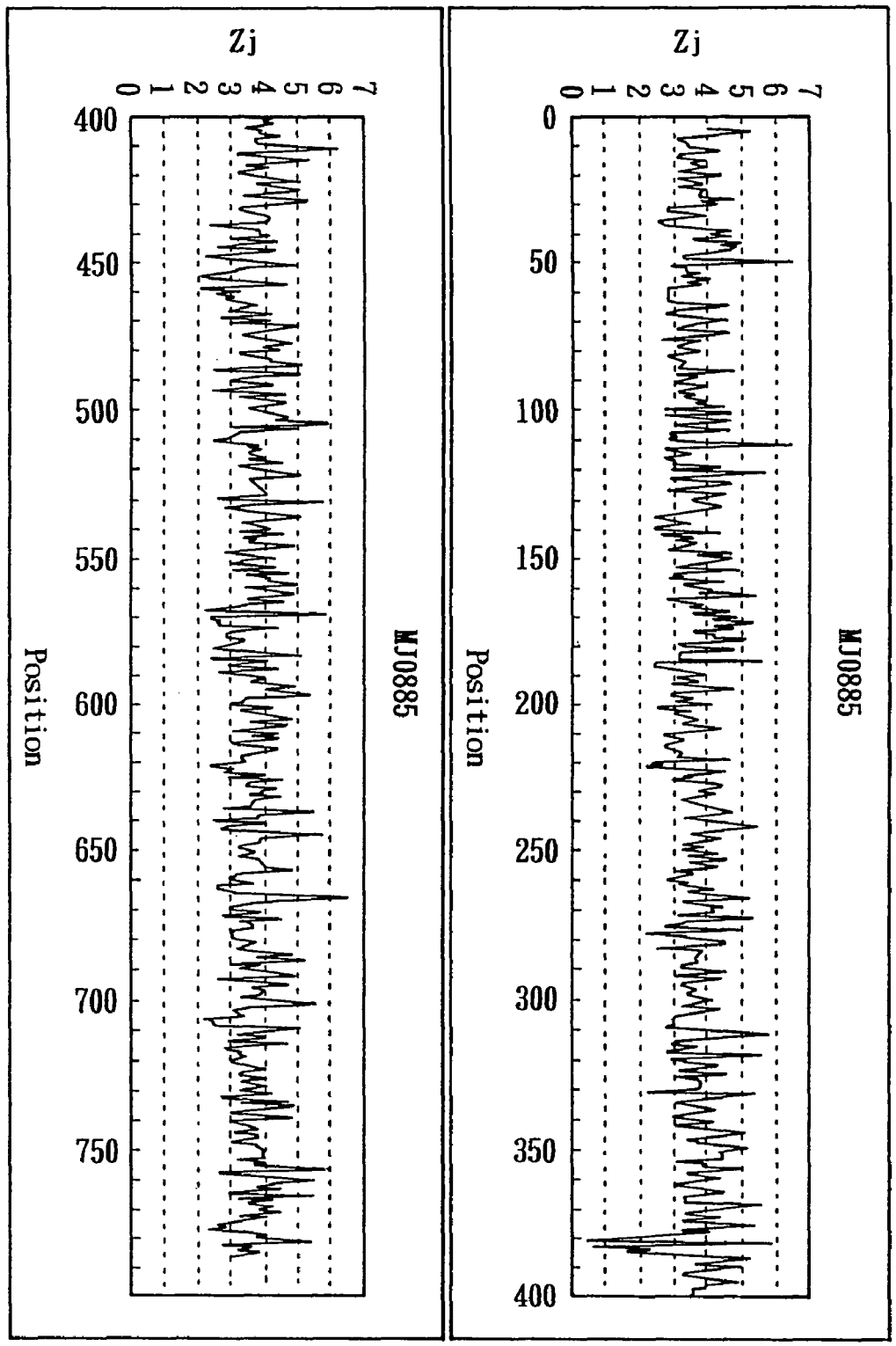
FIG. 14 depicts a distribution chart of the plotted $Zj=-\log Yj$ value for the whole amino acid sequence of the α-type DNA polymerase MJ encoded by MJ0885 (gene name from the genome of *Methanococcus jannaschii*), which value is calculated by the first aspect of the present invention.

According to the method of the first aspect of the present invention and based on the genome data of *Methanococcus jannaschii* (Bult et al., Science 273, 1058-1073, 1996), $Zj=-\log Yj$ (f=-log) was calculated, concerning each amino-acid residue in the amino acid sequence (from the N-terminus to the C terminus) of a DNA polymerase speculated from the microbial gene MJ0885 believed to encode the α-type DNA polymerase. The results are plotted in a distribution chart in FIG. 14.

Figure 15:
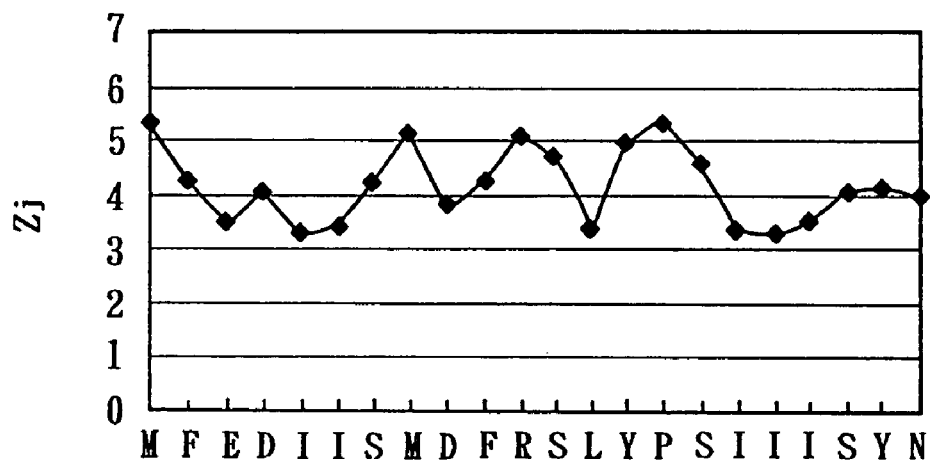
FIG. 15 depicts a distribution chart of the plotted $Zj=-\log Yj$ value for partial sequences (motif A and motif C) of the amino acid sequence of which the distribution chart is shown in FIG. 14.
Figure 15:
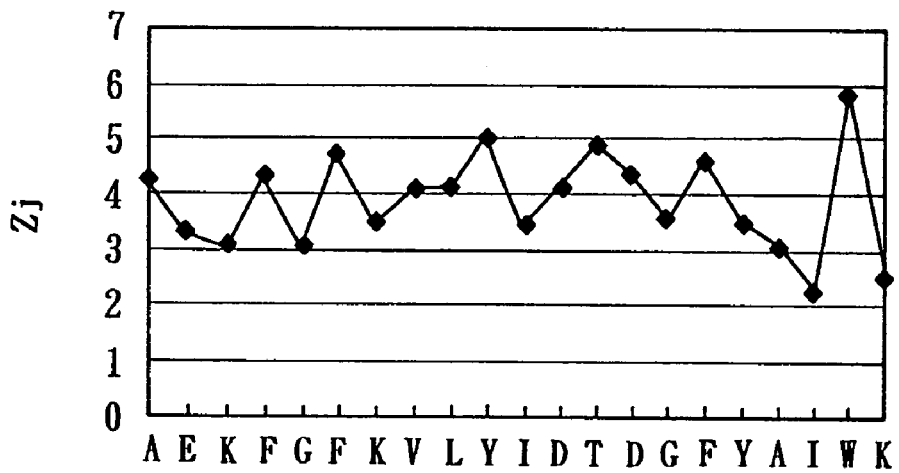
Figure 16:
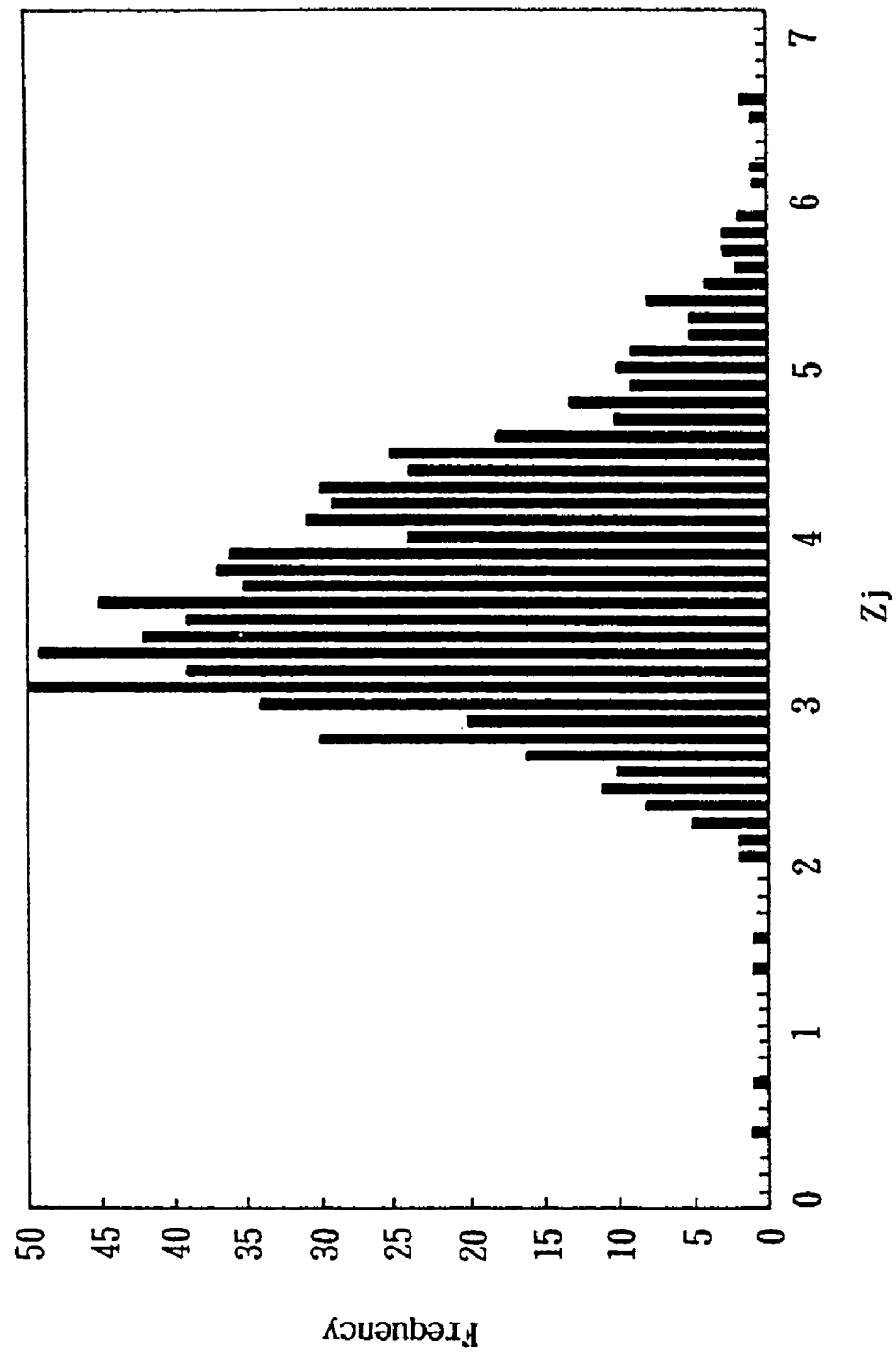
FIG. 16 depicts a frequency distribution chart of the $Zj=-\log Yj$ value calculated on the basis of the amino acid sequence of the α-type DNA polymerase MJ encoded by MJ0885.

Among the motifs known as the functional sites of the α-type DNA polymerase, furthermore, motif A and motif C were extracted, and the Zj values of the individual amino-acid residues were plotted in FIG. 15. FIG. 15 and FIG. 16 below suggest that the $Zj=-\log Yj$ values of amino-acid residues responsible for the function are larger than those of the remaining amino-acid residues:

FIG. 16 depicts a distribution chart of the frequency of the value $Zj=-\log Yj$ for the amino acid sequence of the α-type DNA polymerase encoded by MJ0885. It is confirmed in the figure that amino-acid residues with value $Zj=-\log Yj$ of 4.8 or more are highly possibly amino-acid residues responsible for the protein function.

Example 2

Following the chart on FIG. 15 in Example 1, the characteristic properties of α-type DNA polymerase Pfu (DDBJ Accession No. D12983) derived from *Pyrococcus furious* were modified, on the basis of the amino acid sequence of an α-type DNA polymerase KOD (DDBJ Accession No. D29671) derived from *Pyrococcus* sp., and the genome data of *Methanococcus jannaschii* (Bult et al., Science 273, 1058-1073, 1996), and the amino acid sequence of the α-type DNA polymerase (named here as MJ) encoded by MJ0885.

FIG. 17 depicts alignment charts of the amino acid sequences of the motif Cs from Pfu, KOD and MJ, with no difference between the region 531 to 544 from Pfu and the region 551 to 564 from MJ (the numbers 550 and 570 indicate the N-terminus and C-terminus amino acid residues of the motif C shown here from MJ).

Figure 18:
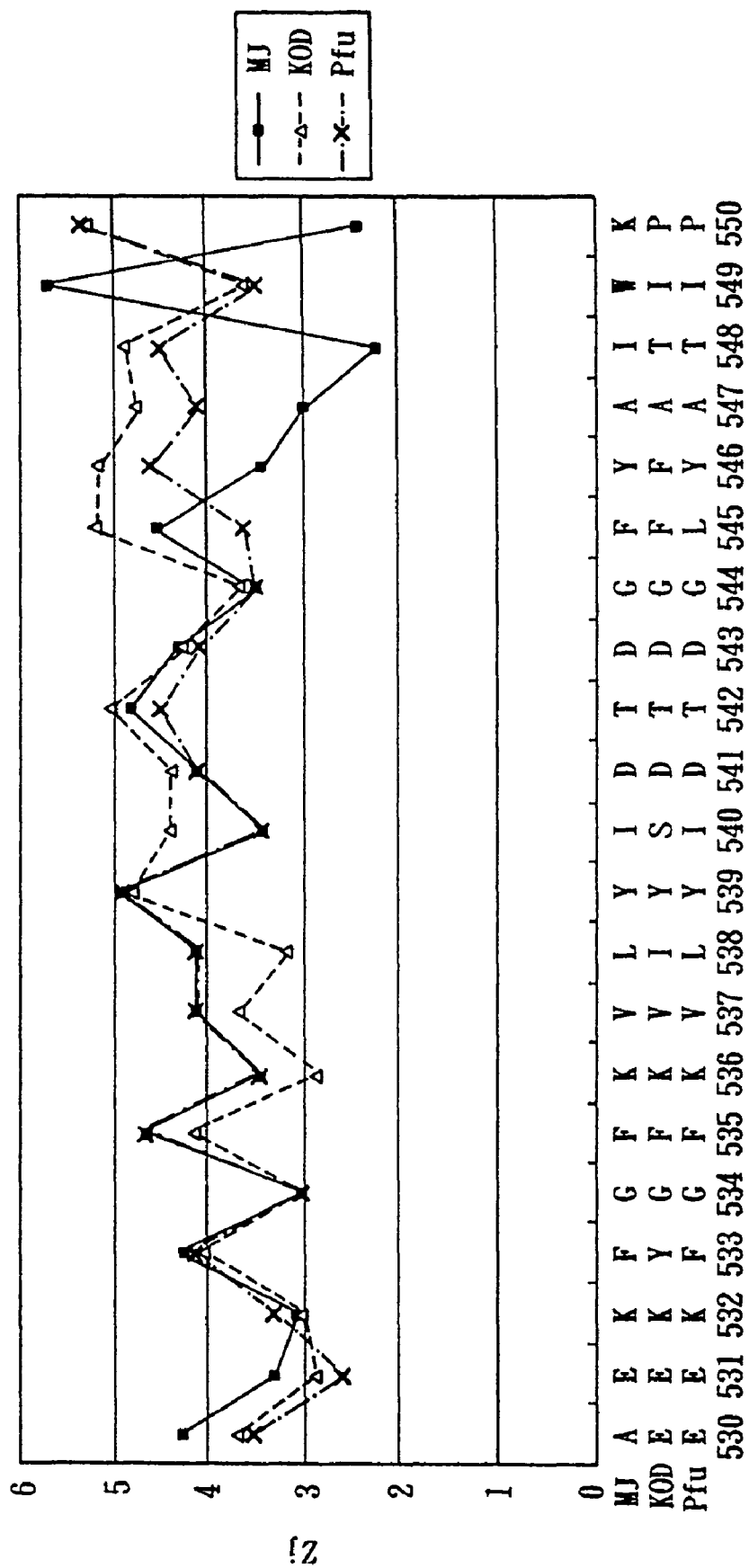
FIG. 18 depicts distribution charts of the plotted $Zj=-\log Yj$ values for the individual motif Cs of the α-type DNA polymerases Pfu, KOD and MJ.

FIG. 18 depicts the results of the prediction of functional sites in the amino acid sequences of the motif Cs of Pfu, KOD and MJ according to the inventive method, on the basis of the genome data of *Methanococcus jannaschii*. The results indicate that mutations Ile540Ser, Leu545Phe, Tyr546Phe, and Ile548Thr increase the $Zj=-\log Yj$ values of the amino-acid residues. Furthermore, the values $Zj=-\log Yj$ of Asp541 and Ala547 are increased. By subjecting the α-type DNA polymerase MJ of *Methanococcus jannaschii* to such mutation, the resulting sequence turns more unique (specific) which possibly brings about the improvement of some function.

Example 3

Based on the genome data of *Methanococcus jannaschii* (Bult et al., Science 273, 1058-1073, 1996), the values $Z(j, 1)=-\log Y(j, 1)$, $Z(j, 3)=-\log Y(j, 3)$, $Z(j, 4)=-\log Y(j, 4)$, and $Z(j, 5)=-\log Y(j, 5)$ were calculated, concerning the individual amino-acid residues of the amino acid sequence (from the N to C termini) of a DNA polymerase speculated on the basis of the microbial gene MJ0885 believed to encode the α-type DNA polymerase, according to the method of the second aspect of the present invention, so that $Wj=Z(j, 3)-Z(j, 1)$ ($h=Z(j, 3)-Z(j, 1)$) was calculated. Similarly, $Wj=Z(j, 4)-Z(j, 3)$ ($h=Z(j, 4)-Z(j, 3)$) and $Wj=Z(j, 5)-Z(j, 3)$ ($h=Z(j, 5)-Z(j, 3)$) were also calculated.

Figure 19:
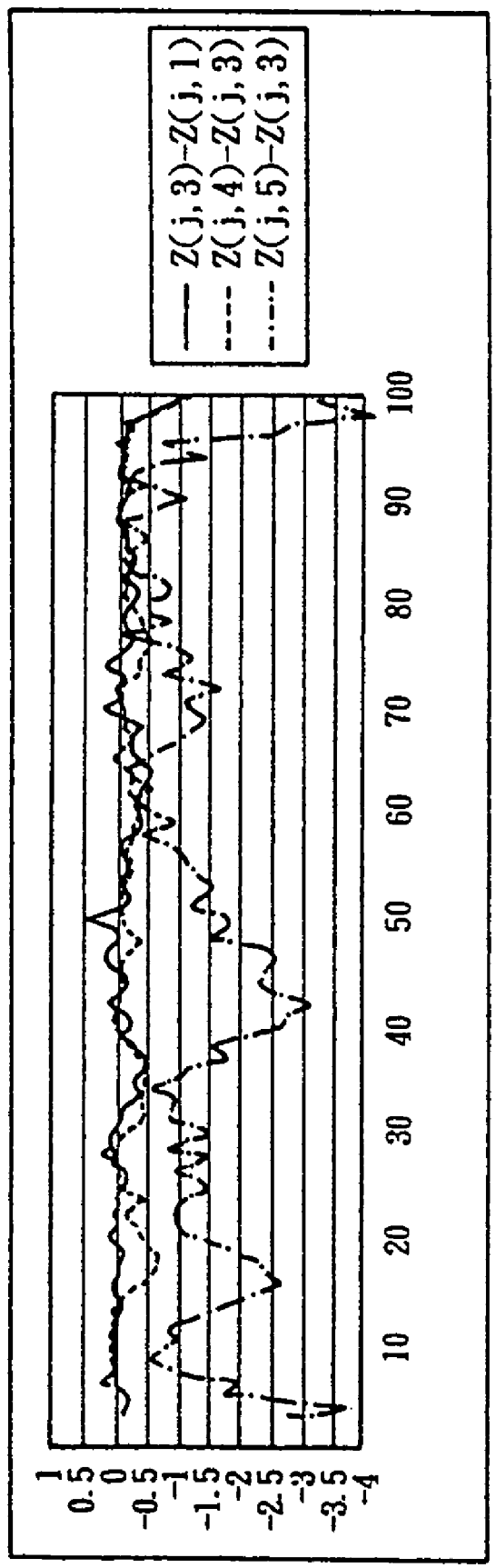
FIG. 19 depicts distribution charts of the plotted values of $Wj=Z(j, 3)-Z(j,1)$ (in solid line), $Wj=Z(j, 4)-Z(j, 3)$ (in dotted line) and $Wj=Z(j, 5)-Z(j, 3)$ (in alternate long and short dash line) of the 100 residues from the N-terminus of the whole amino acid sequence of the α-type DNA polymerase MJ encoded by MJ0885, and these values are calculated by the method of the second aspect of the present invention.

FIG. 19 depicts the results of the 100 residues from the N-terminus in a plotted distribution chart. Given $h=Z(j, 5)-Z(j, 3)$, regions with significantly different distributions from those of the remaining two cases are present in the region from the 35-th to 60-th residues and the like. The distributions indicate that smaller $Wj=Z(j, 5)-(j, 3)$ more specifically characterizes the amino acid sequence.

Figure 20:
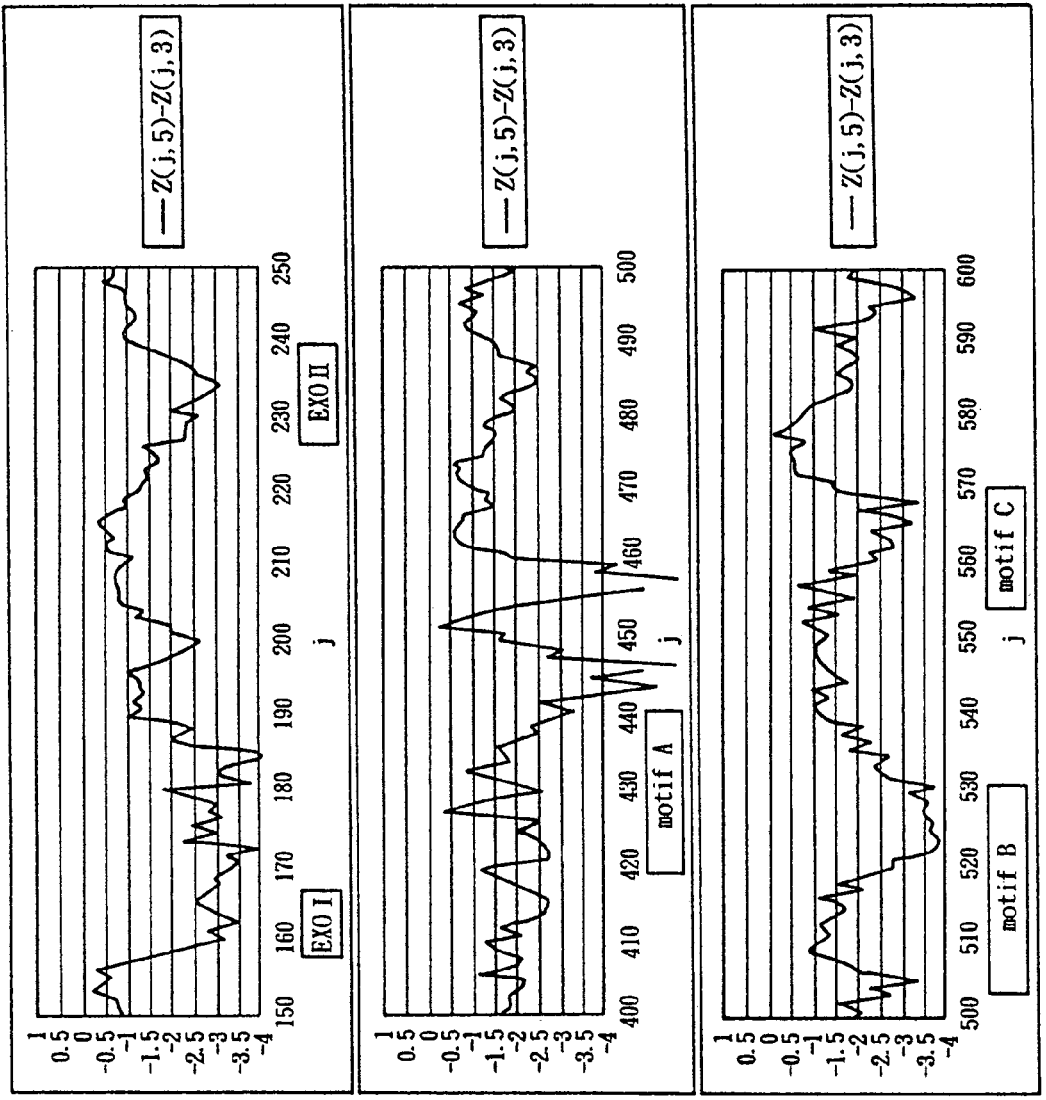
FIG. 20 depicts distribution charts of the plotted value $Wj=Z(j, 5)-Z(j, 3)$ for partial sequences (regions comprising exoI, exoII, motif A, motif B and motif C) of the amino acid sequence of the α-type DNA polymerase MJ encoded by MJ0885.

Among the motifs known as the functional sites of the α-type DNA polymerases, furthermore, regions containing exoI, exoII, motif A, motif B and motif C were extracted, and subsequently, the Wj values of the individual amino-acid residues are plotted in FIG. 20. As shown in FIG. 20, the regions with the characteristic reduction of Wj are consistent with the functional sites.

Example 4

Figure 21:
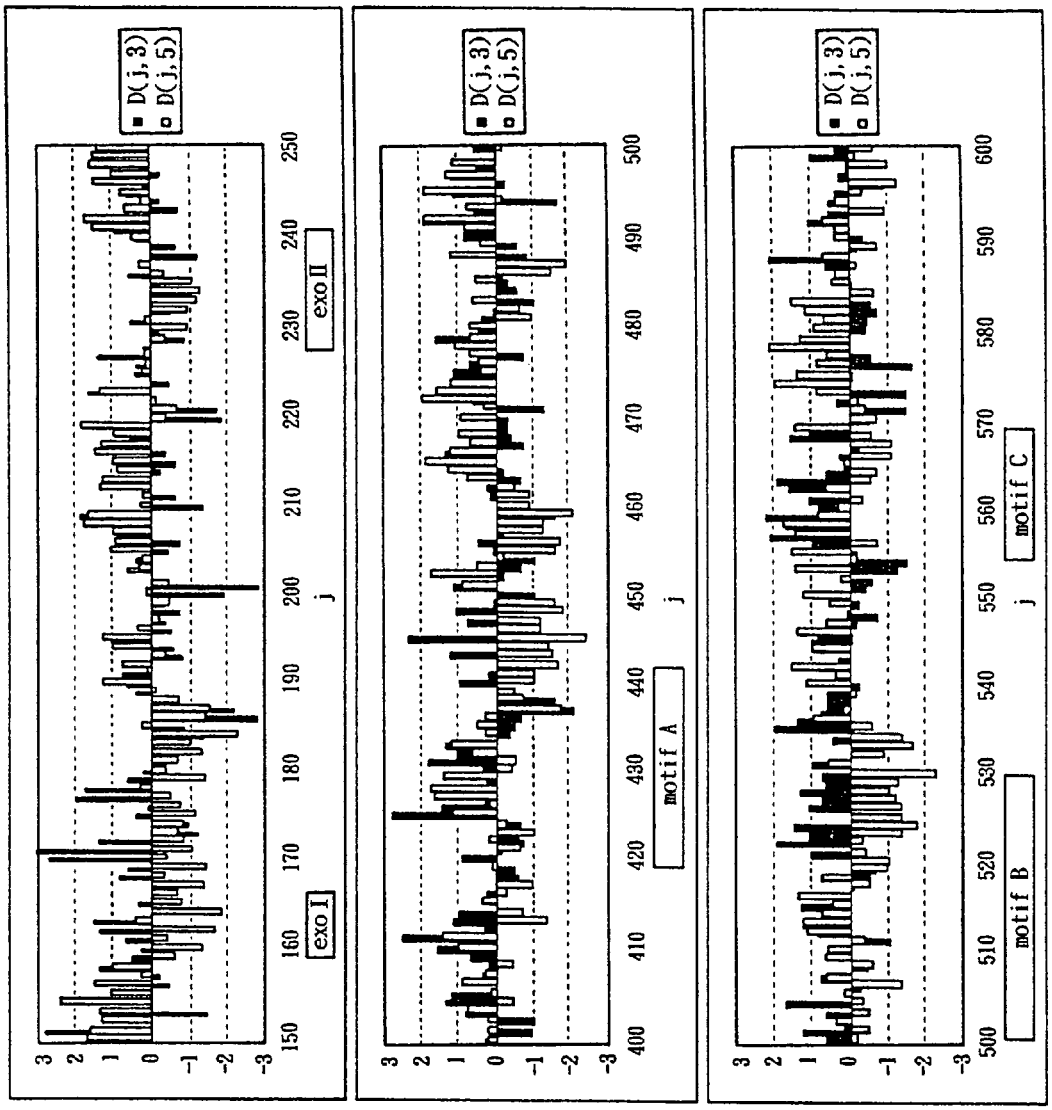
FIG. 21 depicts distribution charts of the plotted values of $Wj=D(j, 3)$ (in dark color) and $Wj=D(j, 5)$ (in pale color) for partial sequences (regions comprising exoI, exoII, motif A, motif B and motif C) of the amino acid sequence of the α-type DNA polymerase MJ encoded by MJ0885.

FIG. 21 depicts the values $Wj=D(j, 3)$ and $Wj=D(j, 5)$ of individual amino-acid residues in the regions containing the exoI, exoII, motif A, motif B and motif C extracted among the motifs known as the functional sites in the α-type DNA polymerases ($h=D(j, 3)$ and $h=D(j, 5)$). Amino-acid residues with $Wj=D(j, n)$ of 2 or more or of 2 or less are present outside the motifs, and these amino-acid residues are candidates of new functional sites.

Example 5

Figure 22:
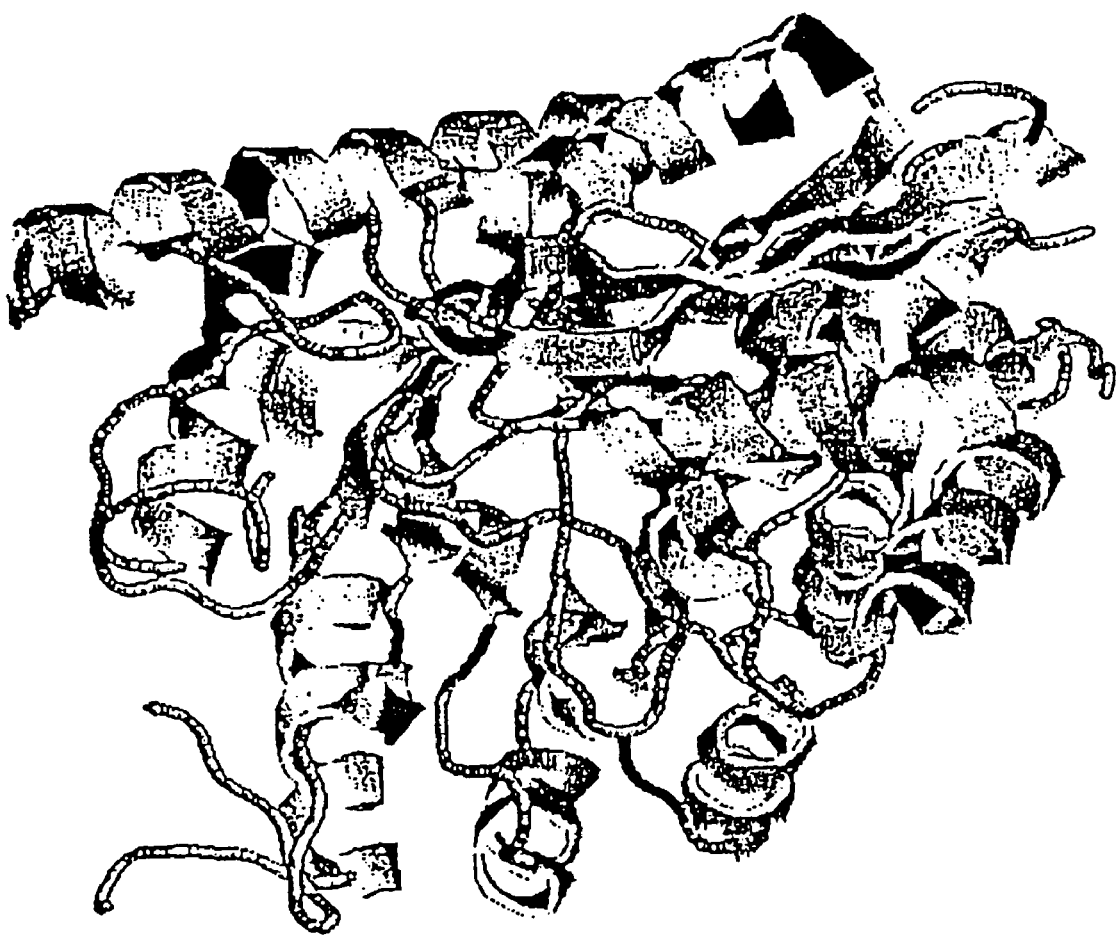
FIG. 22 depicts distribution charts in dark color of the positions of amino-acid residues with $Wj=D(j, 3)$ of 2 or more or of 2 or less in the three-dimensional structure of the amino acid sequence of enolase encoded by MJ0232 (gene name from the genome of *Methanococcus jannaschii*) on a three-dimensional structure model.

FIG. 22 depicts in a dark color the positions of amino-acid residues having $Wj=D(j, 3)$ of 2 or more or of 2 or less in the amino acid sequence of MJ0232, which is speculated as enolase of *Methanococcus jannaschii*, on a three-dimensional structure model prepared on the basis of the enolase of budding yeast. It is indicated that residues positioned apart on the amino acid sequence are closely positioned on the three-dimensional structure.

Example 6

Modified Pfu DNA polymerase I was prepared, by applying the mutation of putative amino-acid residues for improving the function of the DNA polymerase MJ in Example 2 to the Pfu DNA polymerase.

(1) Preparation of Modified Pfu DNA Polymerase Gene

Cloning of Pfu DNA Polymerase Gene:

Following the nucleotide sequence of Pfu DNA polymerase gene (Nucleic Acids Research, Vol. 21, p. 259-265, 1993), a PCR primer was prepared, for amplifying the objective gene by PCR by using the genome DNA of *P. furiosus* as template, which was then cloned in an expression vector for *Escherichia coli*. The detail is described below.

*P. furiosus* DSM3638 was cultured according to the method described in the reference described above. First, the culture medium described in the reference was prepared, followed by sterilization at a high temperature under pressure, and subsequently, nitrogen gas was purged into the resulting culture medium. The bacterium was inoculated into the culture medium, for stationary culturing at 95° C. for 15 hours. From 200 ml of the culture broth were recovered the bacteria of about 0.5 mg by centrifugation. The collected bacteria were suspended in buffer A (10 mM Tris/HCl (pH 8.0) 1 mM EDTA, 100 mM NaCl), followed by addition of 1 ml of 10% SDS and subsequent agitation, and to the resulting suspension was added 0.5 mg of proteinase K for reaction at 55° C. for 60 minutes. The reaction solution was extracted sequentially in phenol, phenol/chloroform, and chloroform, and to the extract was added ethanol to make the DNA insoluble, which was then recovered. The resulting DNA was dissolved in 1 ml of TE buffer (10 mM Tris/HCl (pH 8.0), 1 mM EDTA), followed by addition of 0.5 mg RNase A for reaction at 37° C. for 60 minutes and re-extraction sequentially in phenol, phenol/chloroform, and chloroform, and subsequent ethanol precipitation, to recover the DNA, which was then dissolved in the TE buffer, to recover the DNA at about 0.3 mg.

For PCR amplification of the objective DNA polymerase gene, then, two primer DNAs of SQ ID Nos.2 and 3 were synthesized on the basis of the known sequence data. More specifically, it was designed that the initiation codon ATG of the objective gene and a restriction nuclease NcoI sequence (5'-CCATGG-3') might be introduced in the forward primer sequence, while the reverse primer might be conjugated at an appropriate position downstream the termination codon. PCR was conducted in a reaction system of 50 μl, by using 2 μg of *P. furiosus* DNA and 10 pmol each of the primers under conditions for LA Taq (manufactured by TaKaRa Brewery) and attached buffers. The cycle conditions were as follows; 93° C./3 minutes prior to the addition of the enzyme, and 30 cycles of each cycle composed of 94° C./0.5 minute, 55° C./0.5 minute and 72° C./1.0 minute. The amplified DNA fragment was purified, followed by treatment with NcoI, and the resulting DNA fragment was similarly cleaved with NcoI and subsequently blunt ended, and the resulting fragment was then integrated downstream the T7 promoter of an NcoI-treated expression vector pET-15b. The expression vector was defined as pDPWT100, to confirm the nucleotide sequence of the inserted gene.

Modification of Pfu DNA Polymerase Gene:

According to the known method (Strategies, Vol. 9, p. 3-4, 1996) and for the expression vector pDPWT100 with the cloned Pfu DNA polymerase gene integrated therein, a modified Pfu DNA polymerase gene was prepared on the expression vector pDPWT100 by using oligopeptides containing desired mutations (SQ ID Nos.4 and 5) and the mutation induction kit manufactured by Promega Corporation, whereby an expression vector pDP320 was constructed. By determining the nucleotide sequence of the modified gene, furthermore, the amino acid sequence of the modified Pfu DNA polymerase (SQ ID No.1) was verified.

(2) Expression and Purification of the Modified Pfu DNA Polymerase in *Escherichia coli*

The gene of the modified Pfu DNA polymerase I was expressed in *Escherichia coli* as follows, which was then purified.

The expression vector pDP320 with the modified Pfu DNA polymerase gene was inserted in a strain *Escherichia coli* HMS174 (DE3) and cultured in an LB culture medium supplemented with IPTG to a final concentration of 0.1 mM for 14 hours, to induce the expression of the enzyme in the bacteria of the strain *Escherichia coli*. After harvesting the bacteria by centrifugation, a modified Pfu DNA polymerase was extracted under ultrasonic treatment in a buffer containing 150 mM Tris/HCl (pH 7.5), 2 mM EDTA, 0.24 mM APMSF and 0.2% Tween 20. The crude extract solution was thermally treated at 80° C. for 15 minutes, to inactivate the DNA polymerase derived from *Escherichia coli* and partially purify the DNA polymerase of the present invention. The partially purified fraction was dialyzed against a buffer composed of 50 mM Tris/HCl (pH 7.5), 1 mM EDTA, 0.2% Tween 20, 7 mM 2-mercaptoethanol and 10% glycerol. At the stage was detected a DNA polymerizing activity specific to the modified Pfu DNA polymerase I.

Example 7

By using the modified Pfu DNA polymerase I partially purified in Example 6, the primer elongation reaction of a DNA chain complimentary to the template DNA was tested.

One μg of the partially purified enzyme fraction described above was placed in 20 μl of a reaction solution containing 20 m Tris/HCl(pH 8.0), 2 mM $MgCl_2$, 50 μg/ml BSA, 0.1% Triton X-100, 1 mM each of cold dNTPs (0.1 mM for dCTP), 0.63 μg of pBLUESCRIPT plasmid prepared by annealing together 10 μCi of [α-$^{32}$P]dCTP and a primer of M13(-21), for reaction at 75° C. for one minute and 3 minutes. The elongated DNA chain was separated by electrophoresis on a polyacrylamide gel containing 8M urea, and the resulting pattern was analyzed with an image analyzer. As a control, additionally, the conventional wild-type Pfu DNA polymerase was used for the same DNA synthesis.

Figure 23:
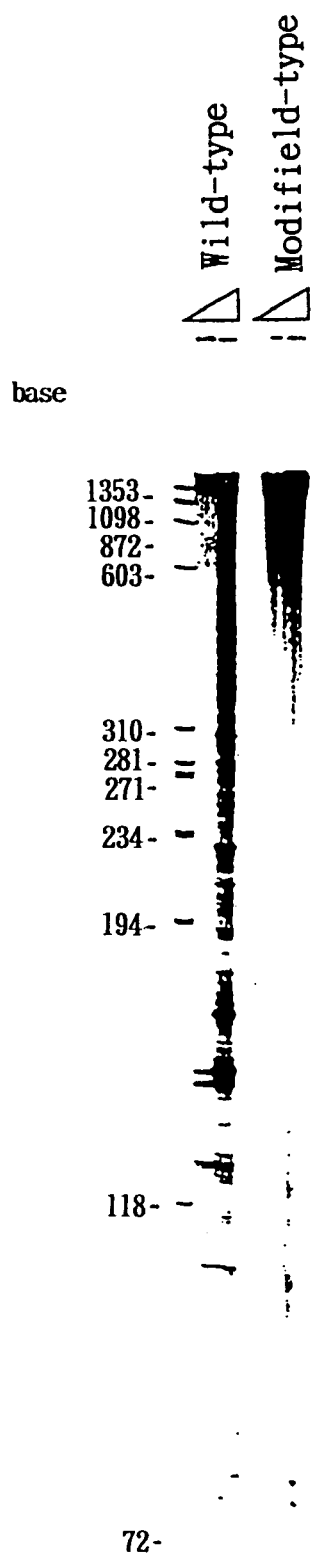
FIG. 23 depicts the results of electrophoresis, indicating the primer elongating activities of the conventional Pfu DNA polymerase (wild type) and the modified Pfu DNA polymerase I of the present invention.

The results are shown in FIG. 23. When the conventional wild-type Pfu DNA polymerase was used, at least 10 bands indicating the presence of incomplete DNA chains due to synthetic termination were observed. However, these bands disappeared during the DNA synthesis with the modified Pfu DNA polymerase I of the present invention. Alternatively, no difference in the accumulation of highly elongated DNA chains around 1000 bases was observed.

Example 8

Pfu DNA polymerases II and III were prepared.

(1) Preparation of Modified Pfu DNA Polymerase Gene

In the same manner as in Example 6(1), the Pfu DNA polymerase gene was cloned, to prepare modified genes II and III as follows.

Preparation of Modified Pfu DNA Polymerase II:

According to the known method (Strategies, Vol. 9, p. 3-4, 1996) and for the expression vector pDPWT100 with the cloned Pfu DNA polymerase gene integrated therein, the gene of modified Pfu DNA polymerase II was prepared on the expression vector pDPWT100 by using oligopeptides containing desired mutations (SQ ID Nos.8 and 9) and the mutation induction kit manufactured by Promega Corporation, whereby an expression vector pDP5b17 was constructed. By determining the nucleotide sequence of the modified gene, furthermore, the amino acid sequence of the modified Pfu DNA polymerase II (SQ ID No.6) was confirmed.

Preparation of the Gene of Modified Pfu DNA Polymerase III:

By the same method as described above except for the use of the oligonucleotides of SQ ID Nos.10 and 11, the gene of modified Pfu DNA polymerase III was prepared, to construct an expression vector pDP5C4. By determining the nucleotide sequence of the modified gene, the amino acid sequence (SQ ID No.7) of the modified Pfu DNA polymerase III was confirmed.

(2) Expression in *Escherichia coli* and Purification of the Modified Pfu DNA Polymerases II and III The genes of the modified Pfu DNA polymerases II and III, thus prepared, were expressed in *Escherichia coli* as follows, which were then purified.

The expression vectors pDP5b17 and pDP5C4 were independently inserted in a strain *Escherichia coli* HMS174 (DE3) and cultured in an LB culture medium supplemented with IPTG to a final concentration of 0.1 mM for 14 hours, to induce the expression of the enzymes in the bacteria of the strain *Escherichia coli*. After harvesting the bacteria by centrifugation, modified Pfu DNA polymerases II and III were extracted, with ultrasonic treatment, in a buffer containing 150 mM Tris/HCl(pH 7.5), 2 mM EDTA, 0.24 mM APMSF and 0.2% Tween 20. The crude extract solution was thermally treated at 80° C. for 15 minutes, to inactivate the DNA polymerases derived from *Escherichia coli* and partially purify the modified DNA polymerases II and III. The partially purified fractions were dialyzed against a buffer composed of 50 mM Tris/HCl (pH 7.5), 1 mM EDTA, 0.2% Tween 20, 7 mM 2-mercaptoethanol and 10% glycerol. At the stage were detected DNA polymerizing activities specific to the modified Pfu DNA polymerases II and III.

Example 9

By using the modified Pfu DNA polymerases II and III partially purified in Example 8, the primer elongation reaction of a DNA chain complimentary to the template DNA was tested.

One μg of each of the partially purified enzyme fractions described above was placed in 20 μl of a reaction solution containing 20 mM Tris/HCl(pH 8.0), 2 mM $MgCl_2$, 50 μg/ml BSA, 0.1% Triton X-100, 1 mM each of cold dNTPs (0.1 mM for dCTP), 0.63 μg of pBLUESCRIPT plasmid prepared by annealing together 10 μCi of [$\alpha$-$^{32}$P]dCTP and a primer M13 (-21), for reaction at 75° C. for one minute and 3 minutes. The elongated DNA chain was separated by electrophoresis on a polyacrylamide gel containing 8M urea, and the resulting pattern was analyzed with an image analyzer. As a control, additionally, the conventional wild-type Pfu DNA polymerase was used for the same DNA synthesis.

Figure 24:
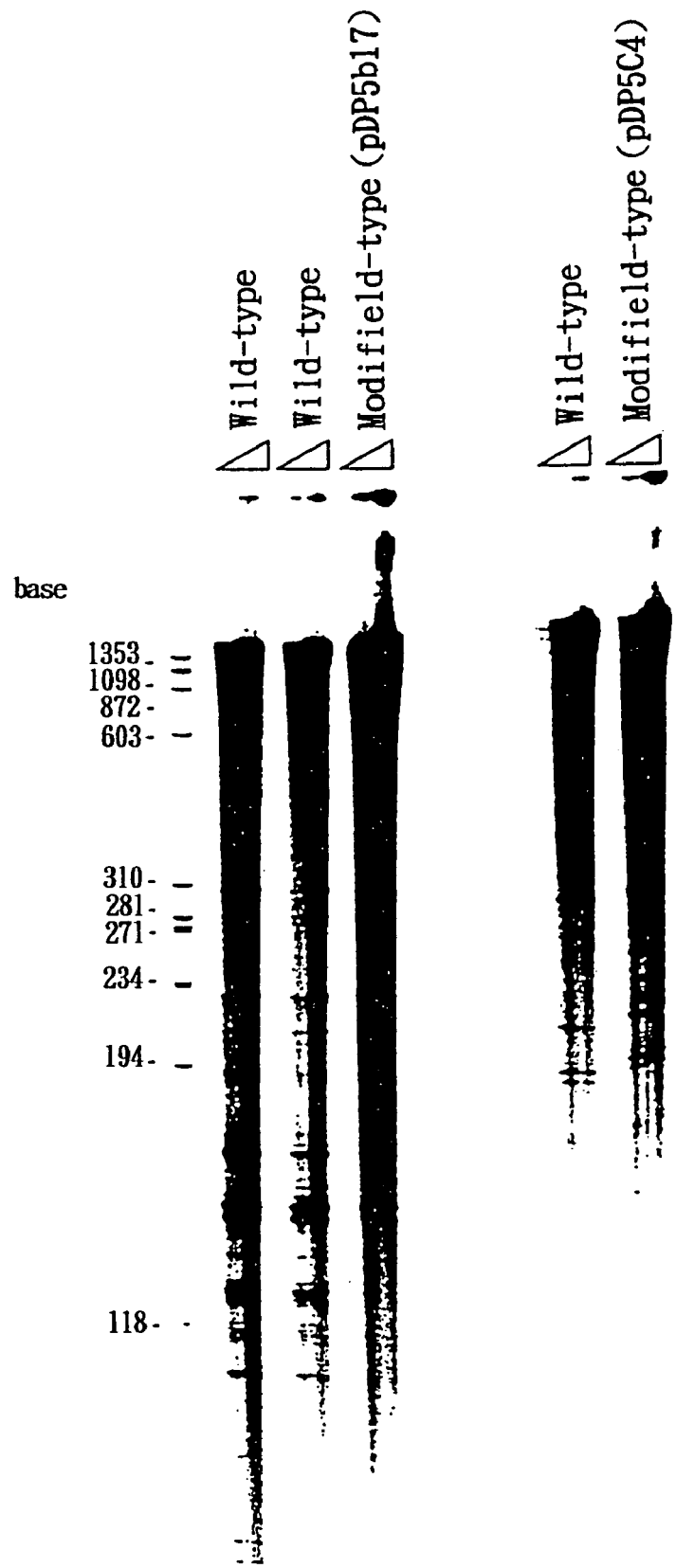
FIG. 24 depicts the results of electrophoresis, indicating the primer elongating activities of the conventional Pfu DNA polymerase (wild type) and the modified Pfu DNA polymerases II and III of the present invention.

The results are shown in FIG. 24. When the conventional wild-type Pfu DNA polymerase was used, bands indicating the presence of incomplete DNA chains were present under observation, because of the presence of a large region at about 1000 bases where synthetic termination occurred. However, the yield of synthesized products including those of bands of about 1000 bases was elevated during the DNA synthesis with the modified Pfu DNA polymerases II and III of the present invention, together with bands indicating the presence of more polymeric (more elongated) PCR products under observation.

The results described above indicate that the DNA polymerases of the present invention can more markedly elongate DNA chains in the course of synthesis during the DNA synthesis by PCR.

INDUSTRIAL APPLICABILITY

In accordance with the present invention, the functional site of a functionally unknown protein recovered by genome analysis or cDNA analysis can be predicted. A novel functional site of a protein with a known function can also be predicted.

The thermophilic DNA polymerases provided by the present invention can highly efficiently synthesize and amplify the whole length of a polymeric DNA by PCR, whereby the in vitro synthesis and amplification of a DNA chain and the nucleotide sequencing thereof can be attained at a high precision in a simple manner.

The invention claimed is:

1. A thermophilic DNA polymerase consisting of the amino acid sequence of SEQ ID NO: 6.

* * * * *

SEQUENCE LISTING

```
<160> NUMBER OF SEQ ID NOS: 19

<210> SEQ ID NO 1
<211> LENGTH: 775
<212> TYPE: PRT
<213> ORGANISM: Unknown
<220> FEATURE:
<223> OTHER INFORMATION: Description of Unknown Organism: DNA polymerase

<400> SEQUENCE: 1

Met Val Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30
```

-continued

```
Thr Phe Arg Pro Tyr Ile Tyr Ala Leu Leu Arg Asp Asp Ser Lys Ile
         35                  40                  45
Glu Glu Val Lys Lys Ile Thr Gly Glu Arg His Gly Lys Ile Val Arg
     50                  55                  60
Ile Val Asp Val Glu Lys Val Glu Lys Phe Leu Gly Lys Pro Ile
 65                  70                  75                  80
Thr Val Trp Lys Leu Tyr Leu Glu His Pro Gln Asp Val Pro Thr Ile
                 85                  90                  95
Arg Glu Lys Val Arg Glu His Pro Ala Val Val Asp Ile Phe Glu Tyr
             100                 105                 110
Asp Ile Pro Phe Ala Lys Arg Tyr Leu Ile Asp Lys Gly Leu Ile Pro
         115                 120                 125
Met Glu Gly Glu Glu Leu Lys Ile Leu Ala Phe Asp Ile Glu Thr
     130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                 165                 170                 175
Asp Leu Pro Tyr Val Glu Val Val Ser Ser Glu Arg Glu Met Ile Lys
             180                 185                 190
Arg Phe Leu Arg Ile Ile Arg Glu Lys Asp Pro Asp Ile Ile Val Thr
         195                 200                 205
Tyr Asn Gly Asp Ser Phe Asp Phe Pro Tyr Leu Ala Lys Arg Ala Glu
     210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                 245                 250                 255
His Phe Asp Leu Tyr His Val Ile Thr Arg Thr Ile Asn Leu Pro Thr
             260                 265                 270
Tyr Thr Leu Glu Ala Val Tyr Glu Ala Ile Phe Gly Lys Pro Lys Glu
     275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                 325                 330                 335
Val Gly Gln Pro Leu Trp Asp Val Ser Arg Ser Ser Thr Gly Asn Leu
             340                 345                 350
Val Glu Trp Phe Leu Leu Arg Lys Ala Tyr Glu Arg Asn Glu Val Ala
         355                 360                 365
Pro Asn Lys Pro Ser Glu Glu Glu Tyr Gln Arg Arg Leu Arg Glu Ser
     370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                 405                 410                 415
His Asn Val Ser Pro Asp Thr Leu Asn Leu Glu Gly Cys Lys Asn Tyr
             420                 425                 430
Asp Ile Ala Pro Gln Val Gly His Lys Phe Cys Lys Asp Ile Pro Gly
         435                 440                 445
Phe Ile Pro Ser Leu Leu Gly His Leu Leu Glu Glu Arg Gln Lys Ile
```

```
            450             455             460
Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Tyr Gly Phe Lys Val Ile Tyr Ser Asp Thr Asp Gly
    530                 535                 540

Phe Phe Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gtggggagca ccatggtttt agatgtggat tacat                              35

<210> SEQ ID NO 3
<211> LENGTH: 35
<212> TYPE: DNA
```

-continued

```
<213> ORGANISM: Artificial Sequence
<220> FEATURE:
<223> OTHER INFORMATION: Description of Artificial Sequence: Synthetic
      DNA

<400> SEQUENCE: 3
gcatgcagat agaccatttc taacgaaggc gtttg                              35

<210> SEQ ID NO 4
<211> LENGTH: 66
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ctcgaagaaa agtatggatt taaagtcatc tacagtgaca ctgatggttt ctttgcaact    60
atccca                                                              66

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
tgggatagtt gcaaagaaac catcagtgtc actgtagatg actttaaatc catactttc     60 ttcgag                                                              66

<210> SEQ ID NO 6
<211> LENGTH: 775
<212> TYPE: PRT
<213> ORGANISM: Unknown
<220> FEATURE:
<223> OTHER INFORMATION: Description of Unknown Organism: DNA polymerase

<400> SEQUENCE: 6

Met Val Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160
```

-continued

```
Ser Tyr Ala Asp Glu Asn Glu Ala Lys Val Ile Thr Trp Lys Asn Ile
                165                 170                 175

Asp Leu Pro Tyr Val Glu Val Val Ser Ser Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
```

-continued

```
                580                 585                 590
Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Arg Ile Arg Asp Arg Ala Ile Pro Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775
```

<210> SEQ ID NO 7
<211> LENGTH: 775
<212> TYPE: PRT
<213> ORGANISM: Unknown
<220> FEATURE:
<223> OTHER INFORMATION: Description of Unknown Organism: DNA polymerase

<400> SEQUENCE: 7

```
Met Val Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
```

-continued

```
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
```

-continued

```
Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Pro Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
agaggcgatg gtcgaattcg cgatagggca attccagctg aggaatacg              49

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
cgtattcctc agctggaatt gccctatcgc gaattcgacc atcgcctct              49

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
ccaattagca atagggcaat tccagctgag gaatacgatc                        40

<210> SEQ ID NO 11
<211> LENGTH: 40
```

-continued

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gatcgtattc ctcagctgga attgccctat tgctaattgg                              40

<210> SEQ ID NO 12
<211> LENGTH: 20
<212> TYPE: PRT
<213> ORGANISM: Artificial Sequence
<220> FEATURE:
<223> OTHER INFORMATION: Synthetic construct

<400> SEQUENCE: 12

Leu Gly Met Ser Met Gly Lys Ile Lys Ile Asp Ala Leu Ile Asp Asn
1               5                   10                  15

Thr Tyr Lys Thr
            20

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: X is any amino acid

<400> SEQUENCE: 13

Gly Met Ser Xaa
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: X is any amino acid

<400> SEQUENCE: 14

Met Ser Xaa Gly
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X is any amino acid

<400> SEQUENCE: 15

Ser Xaa Gly Lys
1

<210> SEQ ID NO 16
```

```
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa Gly Lys Ile
1

<210> SEQ ID NO 17
<211> LENGTH: 21
<212> TYPE: PRT
<213> ORGANISM: Artificial Sequence
<220> FEATURE:
<223> OTHER INFORMATION: Synthetic Construct

<400> SEQUENCE: 17

Ala Glu Lys Phe Gly Phe Lys Val Leu Tyr Ile Asp Thr Asp Gly Phe
1               5                   10                  15

Tyr Ala Ile Trp Lys
            20

<210> SEQ ID NO 18
<211> LENGTH: 21
<212> TYPE: PRT
<213> ORGANISM: Artificial Sequence
<220> FEATURE:
<223> OTHER INFORMATION: Synthetic Construct

<400> SEQUENCE: 18

Glu Glu Lys Tyr Gly Phe Lys Val Ile Tyr Ser Asp Thr Asp Gly Phe
1               5                   10                  15

Phe Ala Thr Ile Pro
            20

<210> SEQ ID NO 19
<211> LENGTH: 21
<212> TYPE: PRT
<213> ORGANISM: Artificial Sequence
<220> FEATURE:
<223> OTHER INFORMATION: Synthetic Construct

<400> SEQUENCE: 19

Glu Glu Lys Phe Gly Phe Lys Val Leu Tyr Ile Asp Thr Asp Gly Leu
1               5                   10                  15

Tyr Ala Thr Ile Pro
            20
```